(12) United States Patent
Fields et al.

(10) Patent No.: US 7,412,977 B2
(45) Date of Patent: Aug. 19, 2008

(54) METHODS AND DEVICES FOR INDUCING COLLAPSE IN LUNG REGIONS FED BY COLLATERAL PATHWAYS

(75) Inventors: Antony J. Fields, San Francisco, CA (US); Ronald Hundertmark, San Mateo, CA (US); John McCutcheon, Menlo Park, CA (US)

(73) Assignee: Emphasys Medical, Inc., Redwood City, CA (US)

( * ) Notice: Subject to any disclaimer, the term of this patent is extended or adjusted under 35 U.S.C. 154(b) by 801 days.

(21) Appl. No.: 10/384,899

(22) Filed: Mar. 6, 2003

(65) Prior Publication Data

US 2003/0228344 A1 Dec. 11, 2003

Related U.S. Application Data

(60) Provisional application No. 60/363,328, filed on Mar. 8, 2002.

(51) Int. Cl.
*A61M 11/00* (2006.01)
(52) U.S. Cl. .............. 128/200.24; 128/207.16; 128/205.24
(58) Field of Classification Search ............ 128/200.24, 128/205.24, 207.14, 207.15, 207.16; 606/213; 604/285; 623/9, 23.65, 23.68, 2.11
See application file for complete search history.

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,788,327 A | 1/1974 | Donowitz et al. | 128/350 |
| 3,874,388 A | 4/1975 | King et al. | 128/334 |
| 4,014,318 A | 3/1977 | Dockum et al. | 128/1 |
| 4,086,665 A | 5/1978 | Poirier | 623/1 |

(Continued)

FOREIGN PATENT DOCUMENTS

EP 0621 015 A1 10/1994

(Continued)

OTHER PUBLICATIONS

Al Jishi et al., "Selective Bronchial Occlusion for Treatment of Bullous Interstitial Emphysema and Bronchopleural Fistula." *J. of Pediatric Surgery*, 29:1545-1547, 1994.

(Continued)

*Primary Examiner*—Steven O. Douglas
(74) *Attorney, Agent, or Firm*—Fish & Richardson P.C.; Fred C. Hernandez

(57) ABSTRACT

Disclosed are methods and devices for regulating fluid flow in one or more lung regions that are supplied fluid through one or more collateral pathways. An identified region of the lung is targeted for volume reduction or collapse. The targeted lung region is then bronchially isolated to inhibit air from flowing into the targeted lung region through bronchial pathways that directly feed air to the targeted lung region. If the targeted lung region does not collapse after bronchially isolating the targeted lung region, then it is possible that a collateral pathway is feeding air to the targeted lung region, thereby preventing the targeted lung region from collapsing. In such a case, the collateral pathway is identified and air flow into the targeted lung region via the collateral pathway is reduced or eliminated.

6 Claims, 21 Drawing Sheets

U.S. PATENT DOCUMENTS

| | | | | |
|---|---|---|---|---|
| 4,212,463 A | 7/1980 | Repinski et al. | ............. | 273/418 |
| 4,250,873 A | 2/1981 | Bonnet | ........ | 600/104 |
| 4,302,854 A | 12/1981 | Runge | ............. | 3/1.7 |
| 4,477,930 A | 10/1984 | Totten et al. | ........ | 3/1.5 |
| 4,710,192 A | 12/1987 | Liotta et al. | ........ | 623/1 |
| 4,732,152 A | 3/1988 | Wallsten et al. | ............. | 128/343 |
| 4,759,758 A | 7/1988 | Gabbay | ........ | 623/2 |
| 4,795,449 A | 1/1989 | Schneider et al. | ........ | 604/329 |
| 4,808,183 A | 2/1989 | Panje | ............. | 623/9 |
| 4,819,664 A | 4/1989 | Nazari | ........ | 128/207.15 |
| 4,830,003 A | 5/1989 | Wolff et al. | ........ | 128/343 |
| 4,832,680 A | 5/1989 | Haber et al. | ........ | 600/31 |
| 4,846,836 A | 7/1989 | Reich | ............. | 623/11 |
| 4,850,999 A | 7/1989 | Planck | ............. | 623/1 |
| 4,852,568 A | 8/1989 | Kensey | ........ | 128/325 |
| 4,877,025 A | 10/1989 | Hanson | ........ | 128/107.16 |
| 4,934,999 A | 6/1990 | Bader | ............. | 600/29 |
| 4,968,294 A | 11/1990 | Salama | ........ | 600/30 |
| 5,061,274 A | 10/1991 | Kensey | ........ | 606/213 |
| 5,116,360 A | 5/1992 | Pinchuk et al. | ........ | 623/1 |
| 5,116,564 A | 5/1992 | Jansen et al. | ........ | 264/255 |
| 5,123,919 A | 6/1992 | Sauter et al. | ........ | 623/2 |
| 5,151,105 A | 9/1992 | Kwan-Gett | ........ | 623/1 |
| 5,161,524 A | 11/1992 | Evans | ........ | 128/203.15 |
| 5,306,234 A | 4/1994 | Johnson | ........ | 604/49 |
| 5,352,240 A | 10/1994 | Ross | ............. | 623/2 |
| 5,358,518 A | 10/1994 | Camilli | ............. | 623/2 |
| 5,366,478 A | 11/1994 | Brinkerhoff et al. | ........ | 660/213 |
| 5,382,261 A | 1/1995 | Palmaz | ........ | 606/158 |
| 5,392,775 A | 2/1995 | Adkins et al. | ........ | 128/207.16 |
| 5,409,019 A | 4/1995 | Wilk | ........ | 128/898 |
| 5,411,507 A | 5/1995 | Heckele | ........ | 606/108 |
| 5,411,552 A | 5/1995 | Andersen et al. | ............. | 623/2 |
| 5,413,599 A | 5/1995 | Imachi et al. | ........ | 623/2 |
| 5,417,226 A | 5/1995 | Juma | ........ | 128/885 |
| 5,445,626 A | 8/1995 | Gigante | ........ | 604/349 |
| 5,486,154 A | 1/1996 | Kelleher | ........ | 600/104 |
| 5,499,995 A | 3/1996 | Teirstein | ........ | 606/192 |
| 5,500,014 A | 3/1996 | Quijano et al. | ........ | 623/2 |
| 5,562,608 A | 10/1996 | Sekins | ........ | 604/20 |
| 5,645,565 A | 7/1997 | Rudd et al. | ........ | 606/213 |
| 5,660,175 A | 8/1997 | Dayal | ........ | 128/207.15 |
| 5,662,713 A | 9/1997 | Andersen et al. | ............. | 623/12 |
| 5,683,451 A | 11/1997 | Lenker et al. | ........ | 623/1 |
| 5,697,968 A | 12/1997 | Rogers et al. | ........ | 623/1 |
| 5,755,770 A | 5/1998 | Ravenscroft | ........ | 623/1 |
| 5,757,593 A | 5/1998 | Stoger | | |
| 5,800,339 A | 9/1998 | Salama | ........ | 600/29 |
| 5,840,081 A | 11/1998 | Andersen et al. | ............. | 623/2 |
| 5,851,232 A | 12/1998 | Lois | ........ | 623/1 |
| 5,855,587 A | 1/1999 | Hyon et al. | ........ | 606/188 |
| 5,855,597 A | 1/1999 | Jayaraman | ........ | 623/1 |
| 5,855,601 A | 1/1999 | Bessler et al. | ........ | 623/2 |
| 5,944,738 A | 8/1999 | Amplatz et al. | ........ | 606/213 |
| 5,947,997 A | 9/1999 | Pavcnik et al. | ........ | 606/213 |
| 5,954,766 A | 9/1999 | Zadno-Azizi et al. | ........ | 623/2 |
| 5,957,949 A | 9/1999 | Leonhardt et al. | ........ | 606/194 |
| 5,976,174 A | 11/1999 | Ruiz | ........ | 606/213 |
| 5,984,965 A | 11/1999 | Knapp et al. | ........ | 623/12 |
| 6,007,575 A | 12/1999 | Samuels | ........ | 623/1 |
| 6,009,614 A | 1/2000 | Morales | ........ | 29/516 |
| 6,016,839 A | 1/2000 | Raftis et al. | | |
| 6,020,380 A | 2/2000 | Killian | ........ | 514/570 |
| 6,022,312 A | 2/2000 | Chaussy et al. | ............. | 600/29 |
| 6,027,525 A | 2/2000 | Suh et al. | ........ | 623/1 |
| 6,051,022 A | 4/2000 | Cai et al. | ........ | 623/2 |
| 6,068,635 A | 5/2000 | Gianotti | ........ | 606/108 |
| 6,068,638 A | 5/2000 | Makower | ........ | 606/159 |
| 6,077,291 A | 6/2000 | Das | ........ | 606/213 |
| 6,083,255 A | 7/2000 | Laufer et al. | ........ | 607/96 |
| 6,123,663 A | 9/2000 | Rebuffat | | |
| 6,135,729 A | 10/2000 | Aber | ........ | 417/420 |
| 6,135,991 A | 10/2000 | Muni et al. | ........ | 604/509 |
| 6,141,855 A | 11/2000 | Morales | ........ | 29/516 |
| 6,162,245 A | 12/2000 | Jayaraman | ........ | 623/1.15 |
| 6,168,614 B1 | 1/2001 | Andersen et al. | ........ | 623/1 |
| 6,174,323 B1 | 1/2001 | Biggs et al. | ........ | 606/232 |
| 6,183,520 B1 | 2/2001 | Pintauro et al. | ........ | 623/23.64 |
| 6,200,333 B1 | 3/2001 | Laufer | ........ | 607/96 |
| 6,206,918 B1 | 3/2001 | Campbell et al. | ........ | 623/2.32 |
| 6,234,996 B1 | 5/2001 | Bagaoisan et al. | ........ | 604/97.01 |
| 6,240,615 B1 | 6/2001 | Kimes et al. | ........ | 29/516 |
| 6,245,102 B1 | 6/2001 | Jayaraman | ........ | 623/1.15 |
| 6,258,100 B1 | 7/2001 | Alferness et al. | ........ | 606/108 |
| 6,270,527 B1 | 8/2001 | Campbell et al. | ........ | 623/2.18 |
| 6,287,290 B1 | 9/2001 | Perkins et al. | ........ | 604/516 |
| 6,293,951 B1 | 9/2001 | Alferness et al. | ........ | 606/108 |
| 6,302,893 B1 | 10/2001 | Limon et al. | ........ | 606/108 |
| 6,312,407 B1 | 11/2001 | Zadno-Azizi et al. | ........ | 604/103.03 |
| 6,325,777 B1 | 12/2001 | Zadno-Azizi et al. | ........ | 604/97.01 |
| 6,325,778 B1 | 12/2001 | Zadno-Azizi et al. | ........ | 604/99.02 |
| 6,327,772 B1 | 12/2001 | Zadno-Azizi et al. | ........ | 29/557 |
| 6,328,689 B1 | 12/2001 | Gonzalez et al. | ........ | 600/37 |
| 6,355,014 B1 | 3/2002 | Zadno-Azizi et al. | ........ | 604/99.02 |
| 6,398,775 B1 | 6/2002 | Perkins et al. | ........ | 604/514 |
| 6,402,754 B1 | 6/2002 | Gonzalez | ........ | 606/69 |
| 6,416,554 B1 | 7/2002 | Alferness et al. | ........ | 623/23.65 |
| 6,458,076 B1 | 10/2002 | Pruitt | ........ | 600/146 |
| 6,485,407 B2 | 11/2002 | Alferness et al. | ........ | 600/37 |
| 6,491,706 B1 | 12/2002 | Alferness et al. | ........ | 606/157 |
| 6,493,589 B1 | 12/2002 | Medhkour et al. | ........ | 607/99 |
| 6,510,846 B1 | 1/2003 | O'Rourke | ........ | 128/200.21 |
| 6,527,761 B1 | 3/2003 | Soltesz et al. | ........ | 604/516 |
| 6,599,311 B1 * | 7/2003 | Biggs et al. | ........ | 606/232 |
| 6,629,951 B2 * | 10/2003 | Laufer et al. | ........ | 604/96.01 |
| 6,712,812 B2 | 3/2004 | Roschak et al. | ........ | 606/41 |
| 6,743,259 B2 * | 6/2004 | Ginn | ........ | 623/23.65 |
| 7,100,616 B2 | 9/2006 | Springmeyer | | |
| 2001/0025132 A1 | 9/2001 | Alferness et al. | ........ | 600/37 |
| 2001/0037808 A1 | 11/2001 | Deem et al. | ........ | 128/200.24 |
| 2001/0041906 A1 | 11/2001 | Gonzalez | ........ | 606/191 |
| 2001/0051799 A1 | 12/2001 | Ingenito | ........ | 604/516 |
| 2001/0052344 A1 | 12/2001 | Doshi | ........ | 128/207 |
| 2001/0056274 A1 | 12/2001 | Perkins et al. | ........ | 604/516 |
| 2002/0007831 A1 | 1/2002 | Davenport et al. | ........ | 128/200.24 |
| 2002/0026233 A1 | 2/2002 | Shaknovich | ........ | 623/1.24 |
| 2002/0062120 A1 | 5/2002 | Perkins et al. | ........ | 604/516 |
| 2002/0077593 A1 | 6/2002 | Perkins et al. | ........ | 604/96.01 |
| 2002/0077696 A1 | 6/2002 | Zadno-Azizi et al. | ........ | 623/1.24 |
| 2002/0087153 A1 | 7/2002 | Roschak et al. | ........ | 606/27 |
| 2002/0095209 A1 | 7/2002 | Zadno-Azizi et al. | ........ | 623/1.24 |
| 2002/0111619 A1 | 8/2002 | Keast et al. | ........ | 606/41 |
| 2002/0111620 A1 | 8/2002 | Cooper et al. | ........ | 606/41 |
| 2002/0112729 A1 | 8/2002 | DeVore et al. | ........ | 128/207.15 |
| 2002/0138135 A1 | 9/2002 | Duerig et al. | ........ | 623/1.24 |
| 2003/0018327 A1 | 1/2003 | Truckai et al. | ........ | 606/32 |
| 2003/0018344 A1 | 1/2003 | Kaji et al. | ........ | 606/130 |
| 2003/0050648 A1 | 3/2003 | Alferness et al. | ........ | 606/108 |
| 2003/0083671 A1 | 5/2003 | Rimbaugh et al. | ........ | 606/108 |
| 2003/0181922 A1 | 9/2003 | Alferness | ........ | 606/108 |
| 2003/0183235 A1 | 10/2003 | Rimbaugh et al. | ........ | 128/207.15 |
| 2004/0073155 A1 | 4/2004 | Laufer et al. | ........ | 604/8 |
| 2004/0073201 A1 | 4/2004 | Cooper et al. | ........ | 606/14 |
| 2006/0200076 A1 | 9/2006 | Gonzalez et al. | | |

FOREIGN PATENT DOCUMENTS

| | | |
|---|---|---|
| EP | 0 621 015 B1 | 10/1994 |
| EP | 1 078 601 A2 | 2/2001 |
| EP | 01/28433 A1 | 4/2001 |
| EP | 1 151 729 A1 | 11/2001 |
| FR | 1309901 | 11/1962 |
| GB | 2324729 | 4/1998 |
| RU | 2140211 | 10/1999 |

| | | |
|---|---|---|
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 A1 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 A1 | 12/1999 |
| WO | 00/15149 | 3/2000 |
| WO | 00/42950 | 7/2000 |
| WO | 00/51510 | 9/2000 |
| WO | 00/62699 | 10/2000 |
| WO | 00/78386 A1 | 12/2000 |
| WO | 00/78407 A1 | 12/2000 |
| WO | 01/02042 A1 | 1/2001 |
| WO | 01/03642 A1 | 1/2001 |
| WO | 01/05334 A1 | 1/2001 |
| WO | 01/10313 A1 | 2/2001 |
| WO | 01/10314 A2 | 2/2001 |
| WO | 01/12104 A1 | 2/2001 |
| WO | 01/13839 A1 | 3/2001 |
| WO | 01/13908 A2 | 3/2001 |
| WO | 01/45590 A2 | 6/2001 |
| WO | 01/54685 A1 | 6/2001 |
| WO | 01/49213 A2 | 7/2001 |
| WO | 01/54585 A1 | 8/2001 |
| WO | 01/54625 A1 | 8/2001 |
| WO | 01/66190 A2 | 9/2001 |
| WO | 01/74271 A1 | 10/2001 |
| WO | 01/87170 A1 | 11/2001 |
| WO | 01/89366 A2 | 11/2001 |
| WO | 01/95786 A2 | 12/2001 |
| WO | 02/05884 A2 | 1/2002 |
| WO | 02/22072 A2 | 3/2002 |
| WO | 02/32333 A1 | 4/2002 |
| WO | 02/34322 A2 | 5/2002 |
| WO | 02/38038 A2 | 5/2002 |
| WO | 02/47575 A2 | 6/2002 |
| WO | 02/056794 A2 | 7/2002 |
| WO | 02/064045 A1 | 8/2002 |
| WO | 02/064190 A2 | 8/2002 |
| WO | 02/064190 A3 | 8/2002 |
| WO | 02/069823 A2 | 9/2002 |
| WO | 02/069823 A3 | 9/2002 |
| WO | 02/094087 A1 | 11/2002 |
| WO | 03/022124 A2 | 3/2003 |
| WO | 03/075796 | 9/2003 |
| WO | 03/079944 | 10/2003 |
| WO | 03/088820 | 10/2003 |
| WO | 03/088912 | 10/2003 |
| WO | 2006/078451 | 7/2006 |

OTHER PUBLICATIONS

Article: "Autocath® 100—Nonsurgical, Intraurethral Bladder Control Device for Incontinent and Retentive Women—Dr. Kulisz's Development", no date.

Derwent citing Russian Patent No. RU 2140211, published Oct. 27, 1999, for: "Method of surgical treatment of patients with pathology of respiratory organs complicated wiht pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc No. 1988-241181/198834 (citing Russian Application No. SU4026409, published Feb. 21, 1986), Russian Patent No. SU 1371700.

Derwent# 008650867 WPI Acc No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919, no date.

Lewis et al., "Pulmonary Interstitial Emphysema: Selective Broncial Occlusion with a Swan-Ganz Catheter", *Archives of Disease in Childhood*, 63:313-315, 1988.

Mathew et al., "Selective bronchial obstruction for treatment of bullous interstitial emphysema", *J. of Ped.*, 96:475-477, 1980.

Okada et al., "Emergent Bronchofiberoptic Bronchial Occlusion for Intractable Pneumothorax with Sever Emphysema", *The Jap. J. of Thor. And Cardio. Sur.*, 46:1078-1081, 1998.

Puhakka et al., "Acute Bronchial Obstruction: An Experimental Rabbit Model Study," *Int. J. of Pediatric Otorhinolaryngology*, 18:107-118, 1989.

Snider et al., *The Definition of Emphysema*: Report of the National Heart Lung and Blood Institute, Division of Lung Diseases Workshop, *Am. Rev. Respir. Dis.*, 132:182-185, 1985.

Woodring et al., "Pneumothorax ex Vacuo", *CHEST*, 100:1102-1124, 1996.

Robbins Pathological Basis of Disease, 5th edition, p. 683, no date.

Raasch BN et al. Radiographic Anatomy of the Interlobar Fissure: A Study of r100 Specimens. AJR 1982; 138:1043-1049.

Morrell NW, et al. Collateral Ventilation and Gas Exchange in Emphysema, Am J Respir Crit Care Med 1994;150:635-41.

* cited by examiner

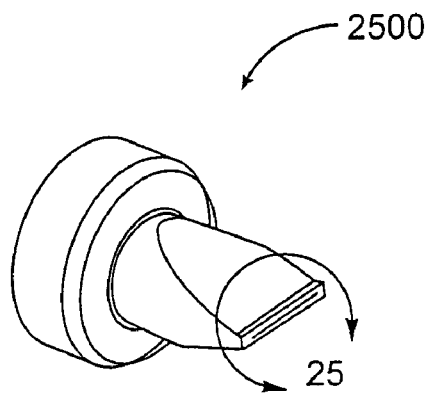
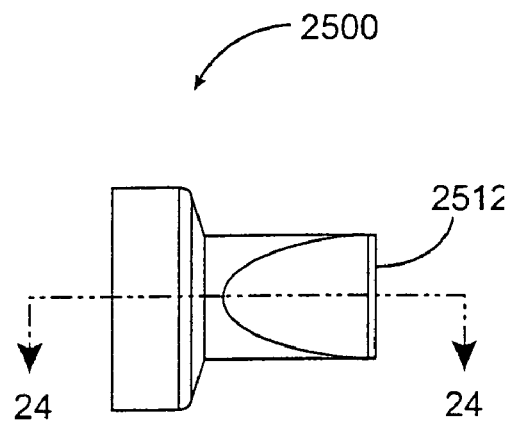
FIG. 22                FIG. 23
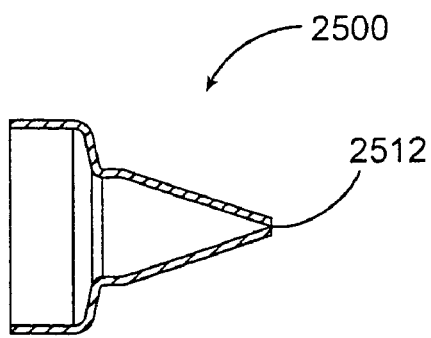
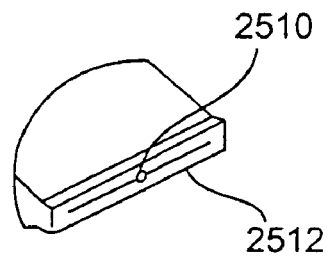
FIG. 24                FIG. 25

METHODS AND DEVICES FOR INDUCING COLLAPSE IN LUNG REGIONS FED BY COLLATERAL PATHWAYS

REFERENCE TO PRIORITY DOCUMENT

This application claims priority of U.S. Provisional Patent Application Ser. No. 60/363,328 entitled "Methods and Devices for Inducing Collapse in Lung Regions Fed by Collateral Pathways" by A. Fields et al., filed Mar. 8, 2002. Priority of the filing date of Mar. 8, 2002 is hereby claimed, and the disclosure of the Provisional Patent Application is hereby incorporated by reference.

BACKGROUND OF THE INVENTION

1. Field of the Invention

This invention relates generally to methods and devices for use in performing pulmonary procedures and, more particularly, to procedures for treating various diseases of the lung.

2. Description of the Related Art

Pulmonary diseases such as chronic obstructive pulmonary disease (COPD) reduce the ability of one or both lungs to fully expel air during the exhalation phase of the breathing cycle. The term "Chronic Obstructive Pulmonary Disease" (COPD) refers to a group of diseases that share a major symptom, dyspnea. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema. While each has distinct anatomic and clinical considerations, many patients may have overlapping characteristics of damage at both the acinar (as seen in emphysema) and the bronchial (as seen in bronchitis) levels, almost certainly because one pathogenic mechanism—cigarette smoking is common to both. (Robbins Pathological Basis of Disease, $5^{th}$ edition, pg 683)

Emphysema is a condition of the lung characterized by the abnormal permanent enlargement of the airspaces distal to the terminal bronchiole, accompanied by the destruction of their walls, and without obvious fibrosis. It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli (the air sacs where oxygen-carbon dioxide exchange occurs). This tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange. One way of deflating the diseased portion of the lung is to applying suction to these narrow airways. However, such suction may undesirably collapse the airways, especially the more proximal airways, due to the surrounding diseased tissue, thereby preventing successful fluid removal.

In addition, hyper-expanded lung tissue occupies more of the pleural space than healthy lung tissue. In most cases, a portion of the lung is diseased while the remaining part is relatively healthy and therefore still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent, healthier tissue.

Lung volume reduction surgery is a conventional method of treating lung diseases such as emphysema. According to the lung reduction procedure, a diseased portion of the lung is surgically removed, which makes more of the pleural space available to accommodate the functioning, healthier portions of the lung. The lung is typically accessed through a median sternotomy or lateral thoracotomy. A portion of the lung, typically the upper lobe of each lung, is freed from the chest wall and then resected, e.g., by a stapler lined with bovine pericardium to reinforce the lung tissue adjacent the cut line and also to prevent air or blood leakage. The chest is then closed and tubes are inserted to remove fluid from the pleural cavity. The conventional surgical approach is relatively traumatic and invasive, and, like most surgical procedures, is not a viable option for all patients.

Some recently proposed treatments include the use of devices that isolate a diseased region of the lung in order to reduce the volume of the diseased region, such as by collapsing the diseased lung region. According to such treatments, isolation devices are implanted in airways feeding the targeted region of the lung to isolate the region of the lung targeted for volume reduction or collapse. These implanted isolation devices can be, for example, one-way valves that allow flow in the exhalation direction only, occluders or plugs that prevent flow in either direction, or two-way valves that control flow in both directions. However, even with the implanted isolation devices properly deployed, air can flow into the isolated lung region via a collateral pathway. This can result in the diseased region of the lung still receiving air even though the isolation devices were implanted into the direct pathways to the lung. Collateral flow can be, for example, air flow that flows between segments of a lung, or it can be, for example, air flow that flows between lobes of a lung, as described in more detail below.

Collateral flow into an isolated lung region can make it difficult to achieve a desired flow dynamic for the lung region. Moreover, it has been shown that as the disease progresses, the collateral flow throughout the lung can increase, which makes it even more difficult to properly isolate a diseased lung region by simply implanting flow control valves in the bronchial passageways that directly feed air to the diseased lung region.

In view of the foregoing, there is a need for a method and device for regulating fluid flow to and from a region of a lung that is supplied air through a collateral pathway, such as to achieve a desired flow dynamic or to induce collapse in the lung region.

SUMMARY

Disclosed are methods and devices for regulating fluid flow to and from a lung region that is supplied air through one or more collateral pathways, such as to induce collapse in the lung region or to achieve a desired flow dynamic. In accordance with one aspect of the invention, there is disclosed a method of regulating fluid flow for a targeted lung region, comprising identifying at least one collateral pathway that provides collateral fluid flow into the targeted lung region and performing an intervention within the lung to reduce the amount of collateral fluid flow provided to the targeted lung region through the collateral pathway. The method can also include identifying at least one direct pathway that provides direct fluid flow into the targeted lung region and deploying a bronchial isolation device in the direct pathway to regulate fluid flow to the targeted lung region through the direct pathway.

Also disclosed is a method of regulating fluid flow for a targeted lung region, comprising reducing direct fluid flow in a direct pathway that provides direct fluid flow to the targeted lung region; and reducing collateral fluid flow that flows through a collateral pathway to the targeted lung region.

Other features and advantages of the present invention should be apparent from the following description of various embodiments, which illustrate, by way of example, the principles of the invention.

BRIEF DESCRIPTION OF THE DRAWINGS

FIG. 22 shows a a valve element.

FIG. 23 shows a side view of the valve element of FIG. 22.

FIG. 24 shows a cross-sectional view of the valve element of FIG. 22 along the line 24-24 of FIG. 23.

FIG. 25 shows an enlarged, sectional view of the portion of the flow control element contained within line 25 of FIG. 22.

DETAILED DESCRIPTION

Unless defined otherwise, all technical and scientific terms used herein have the same meaning as is commonly understood by one of skill in the art to which the invention(s) belong.

Disclosed are methods and devices for regulating fluid flow to and from a region of a patient's lung, such as to achieve a desired fluid flow dynamic to a lung region during respiration and/or to induce collapse in one or more lung regions that are supplied air through one or more collateral pathways. An identified region of the lung (referred to herein as the "targeted lung region") is targeted for flow regulation, such as to achieve volume reduction or collapse. The targeted lung region is then bronchially isolated to regulate fluid flow to the targeted lung region through bronchial pathways that directly feed fluid to the targeted lung region. If a desired flow characteristic to the targeted region is not achieved, or if the targeted lung region does not collapse after bronchially isolating the targeted lung region, then it is possible that a collateral pathway is feeding air to the targeted lung region. The collateral flow can prevent the targeted lung region from collapsing. In such a case, the collateral pathway is identified and an intervention is performed within the lung to modify or inhibit fluid flow into the targeted lung region via the collateral pathway, such as according to the methods described herein. While the invention can involve such treatment of collateral flow pathways in combination with bronchial isolation, it should be understood that the invention may also be practiced without bronchial isolation in some circumstances. Further, the invention also encompasses temporary bronchial isolation while treating lung regions fed by collateral pathways.

Exemplary Lung Regions

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer, for example, to a lung lobe or a lung segment. Such nomenclature conform to nomenclature for portions of the lungs that are known to those skilled in the art. However, it should be appreciated that the term lung region does not necessarily refer to a lung lobe or a lung segment, but can refer to some other defined division or portion of a human or non-human lung.

Figure 1:
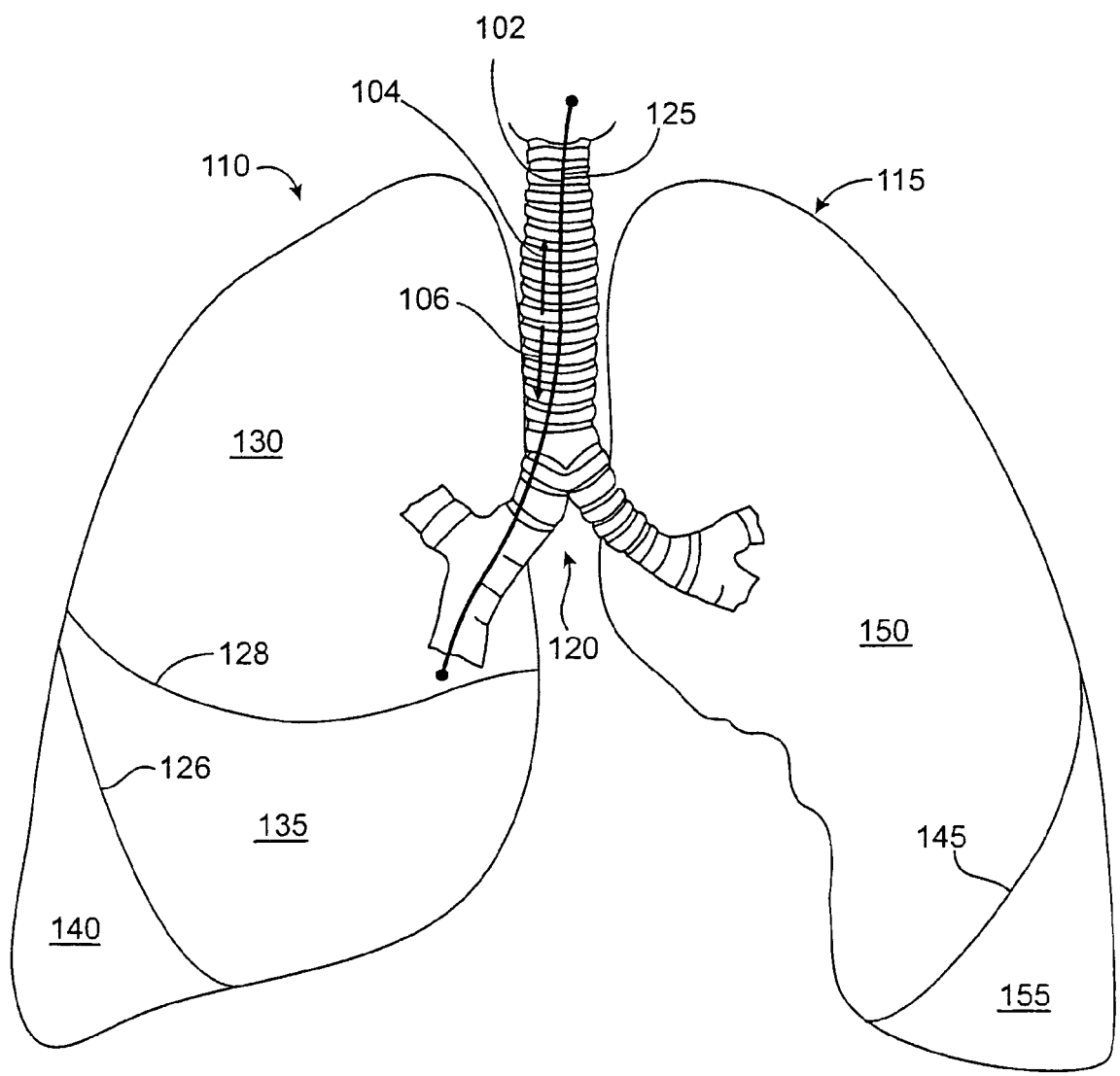
FIG. 1 illustrates an anterior view of a pair of human lungs and a bronchial tree.

FIG. 1 shows an anterior view of a pair of human lungs 110, 115 and a bronchial tree 120 that provides a fluid pathway into and out of the lungs 110, 115 from a trachea 125, as will be known to those skilled in the art. As used herein, the term "fluid" can refer to a gas, a liquid, or a combination of gas(es) and liquid(s). For clarity of illustration, FIG. 1 shows only a portion of the bronchial tree 120, which is described in more detail below with reference to FIG. 4.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 1 shows a path 102 that travels through the trachea 125 and through a bronchial passageway into a location in the right lung 110. The term "proximal direction" refers to the direction along such a path 102 that points toward the patient's mouth or nose and away from the patient's lungs. In other words, the proximal direction is generally the same as the expiration direction when the patient breathes. The arrow 104 in FIG. 1 points in the proximal or expiratory direction. The term "distal direction" refers to the direction along such a path 102 that points toward the patient's lung and away from the mouth or nose. The distal direction is generally the same as the inhalation or inspiratory direction when the patient breathes. The arrow 106 in FIG. 1 points in the distal or inhalation direction.

The lungs include a right lung 110 and a left lung 115. The right lung 110 includes lung regions comprised of three lobes, including a right upper lobe 130, a right middle lobe 135, and a right lower lobe 140. The lobes 130, 135, 140 are separated by two interlobar fissures, including a right oblique fissure 126 and a right transverse fissure 128. The right oblique fissure 126 separates the right lower lobe 140 from the right upper lobe 130 and from the right middle lobe 135. The right transverse fissure 128 separates the right upper lobe 130 from the right middle lobe 135.

As shown in FIG. 1, the left lung 115 includes lung regions comprised of two lobes, including the left upper lobe 150 and the left lower lobe 155. An interlobar fissure comprised of a left oblique fissure 145 of the left lung 115 separates the left upper lobe 150 from the left lower lobe 155. The lobes 130, 135, 140, 150, 155 are directly supplied air via respective lobar bronchi, as described in detail below.

Figure 2:
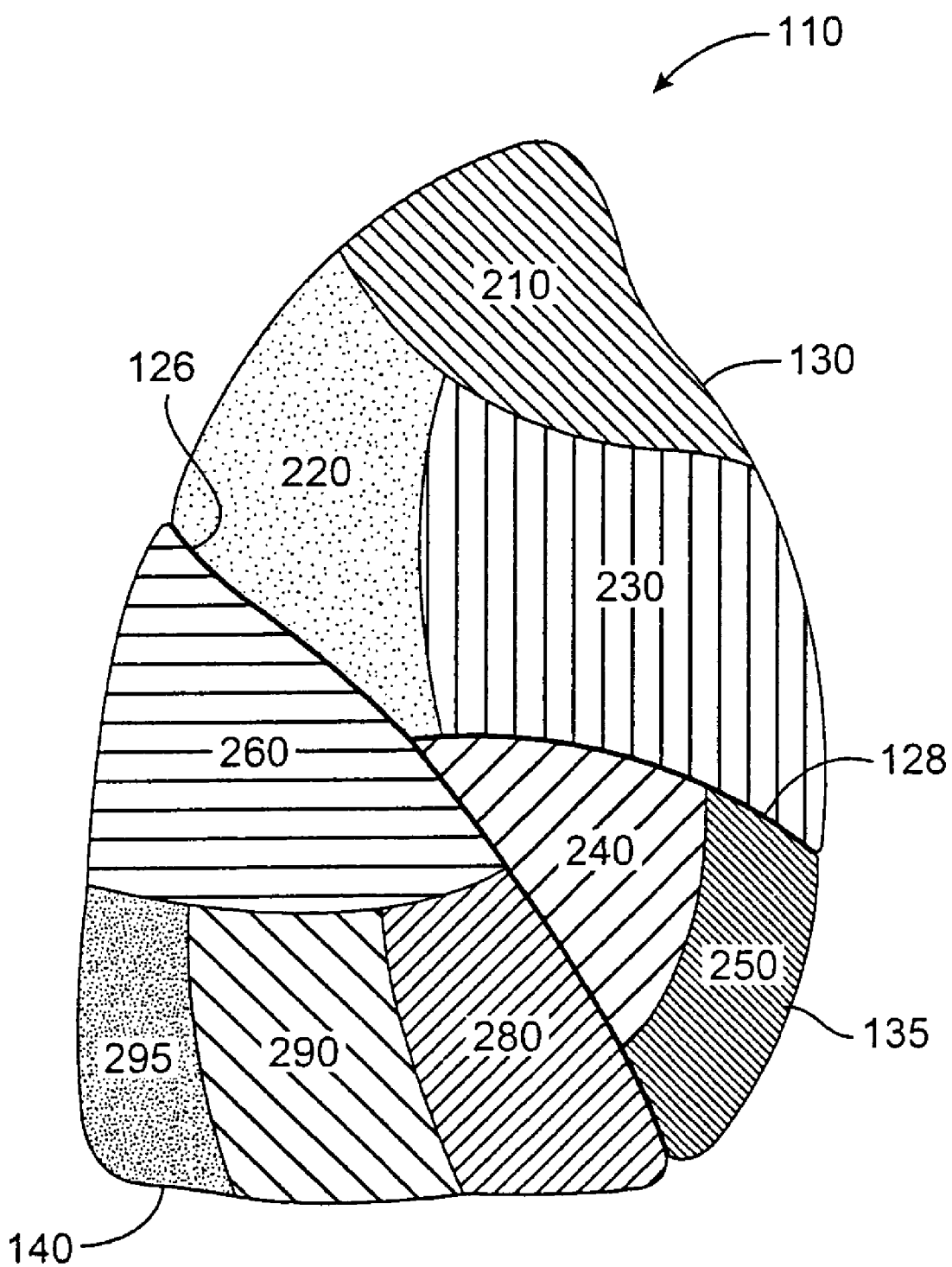
FIG. 2 illustrates a lateral view of the right lung.

FIG. 2 is a lateral view of the right lung 110. The right lung 110 is subdivided into lung regions comprised of a plurality of bronchopulmonary segments. Each bronchopulmonary segment is directly supplied air by a corresponding segmental tertiary bronchus, as described below. The bronchopulmonary segments of the right lung 110 include a right apical segment 210, a right posterior segment 220, and a right anterior segment 230, all of which are disposed in the right upper lobe 130. The right lung bronchopulmonary segments further include a right lateral segment 240 and a right medial segment 250, which are disposed in the right middle lobe 135. The right lower lobe 140 includes bronchopulmonary segments comprised of a right superior segment 260, a right medial basal segment (which cannot be seen from the lateral view and is not shown in FIG. 2), a right anterior basal segment 280, a right lateral basal segment 290, and a right posterior basal segment 295.

Figure 3:
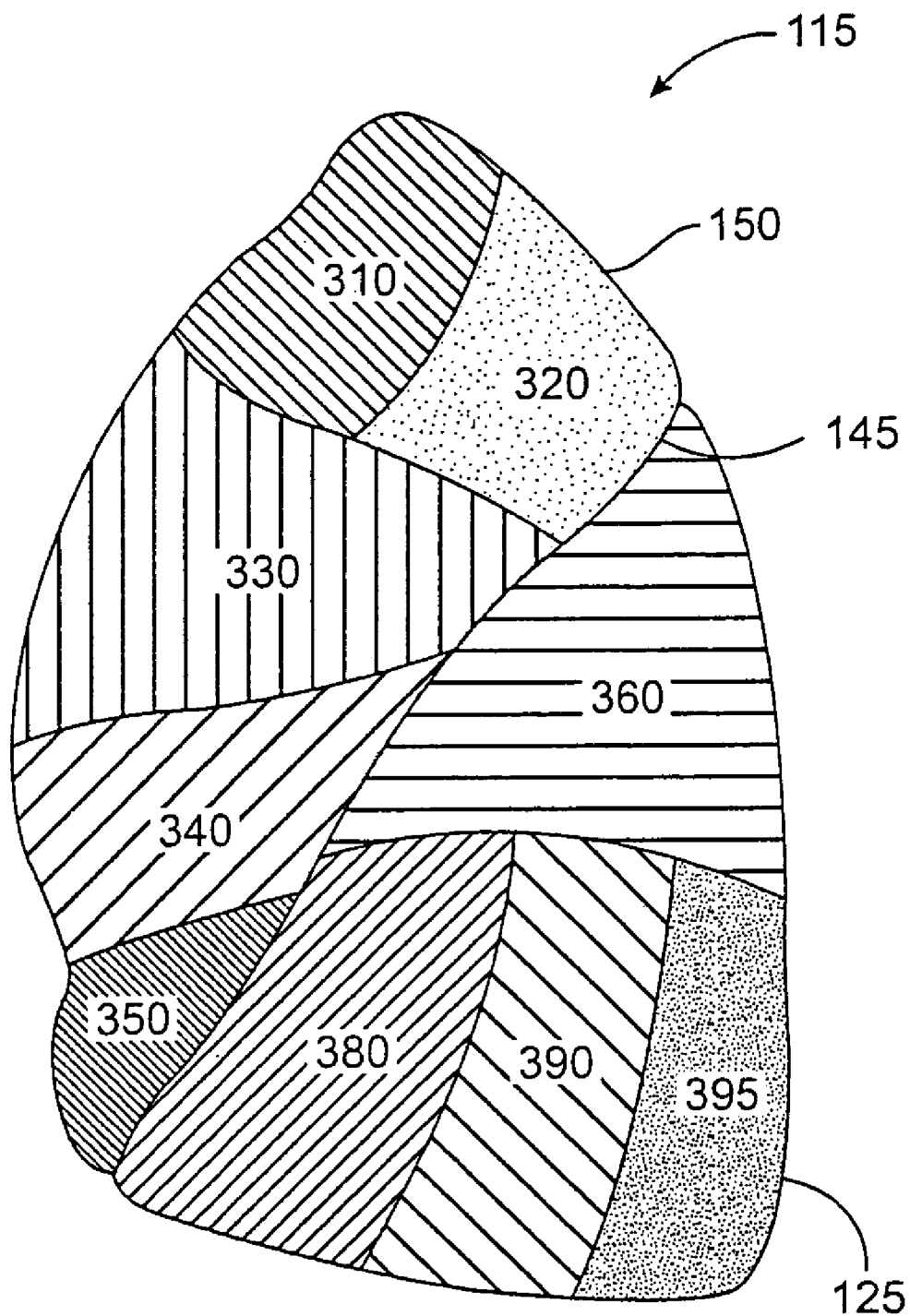
FIG. 3 illustrates a lateral view of the left lung.

FIG. 3 shows a lateral view of the left lung 115, which is subdivided into lung regions comprised of a plurality of bronchopulmonary segments. The bronchopulmonary segments include a left apical segment 310, a left posterior segment 320, a left anterior segment 330, a left superior segment 340, and a left inferior segment 350, which are disposed in the left lung upper lobe 150. The lower lobe 155 of the left lung 115 includes bronchopulmonary segments comprised of a left superior segment 360, a left medial basal segment (which cannot be seen from the lateral view and is not shown in FIG. 3), a left anterior basal segment 380, a left lateral basal segment 390, and a left posterior basal segment 395.

Figure 4:
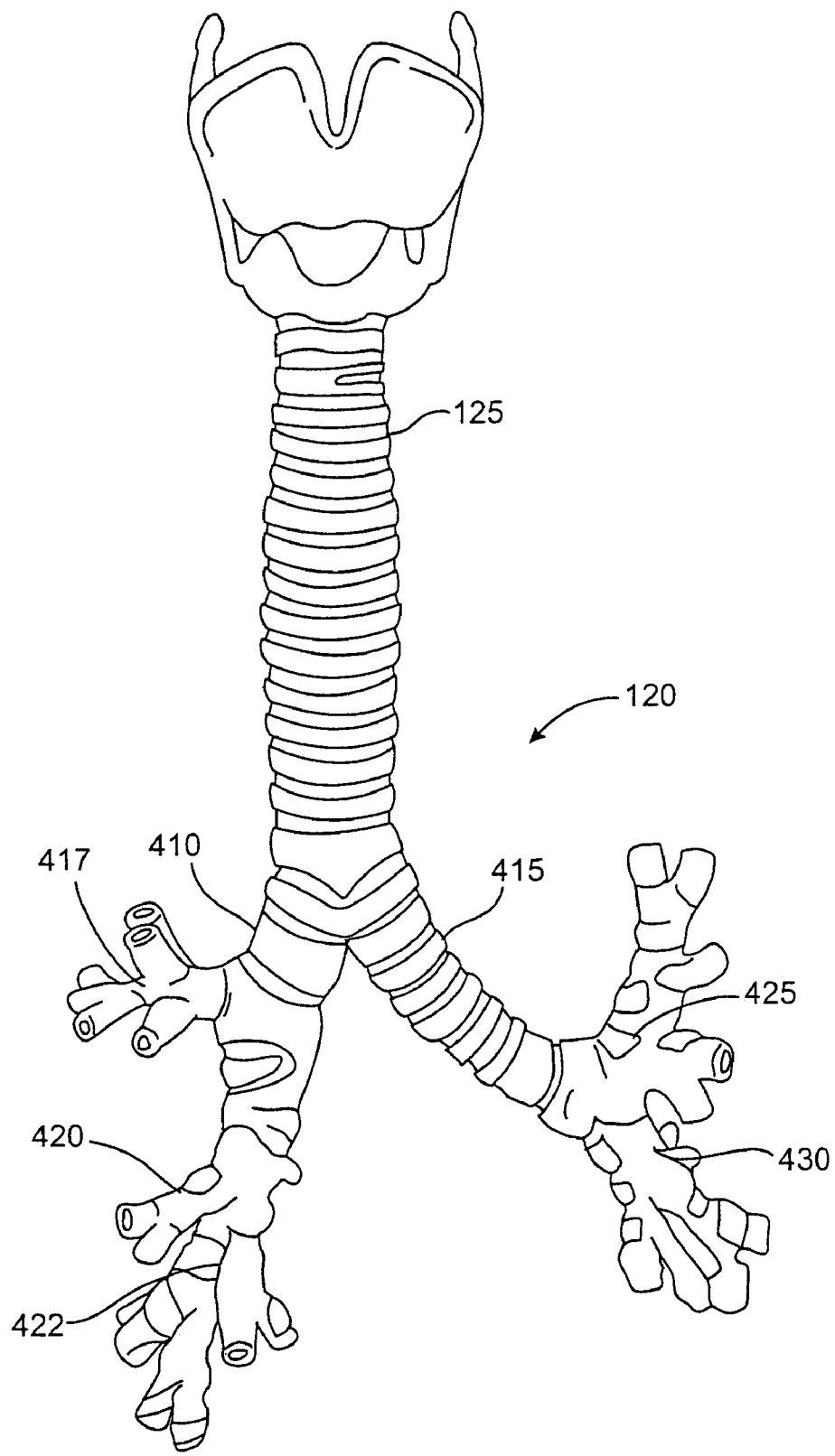
FIG. 4 illustrates an anterior view of the trachea and a portion of the bronchial tree.

FIG. 4 shows an anterior view of the trachea 125 and a portion of the bronchial tree 120, which includes a network of bronchial passageways, as described below. In the context of describing the lung, the terms "pathway" and "lumen" are used interchangeably herein. The trachea 125 divides at a lower end into two bronchial passageways comprised of primary bronchi, including a right primary bronchus 410 that provides direct air flow to the right lung 110, and a left primary bronchus 415 that provides direct air flow to the left lung 115. Each primary bronchus 410, 415 divides into a next generation of bronchial passageways comprised of a plurality of lobar bronchi. The right primary bronchus 410 divides into a right upper lobar bronchus 417, a right middle lobar bronchus 420, and a right lower lobar bronchus 422. The left primary bronchus 415 divides into a left upper lobar bronchus 425 and a left lower lobar bronchus 430. Each lobar bronchus, 417, 420, 422, 425, 430 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Direct and Collateral Flow

Throughout this disclosure, reference is made to a "direct pathway" to a targeted lung region and to a "collateral pathway" to a targeted lung region. The term "direct pathway" refers to a bronchial passageway that branches directly or indirectly from the trachea and either (1) terminates in the targeted lung region to thereby directly provide air to the targeted lung region; or (2) branches into at least one other bronchial passageway that terminates in the targeted lung region to thereby directly provide air to the targeted lung region. The term "collateral pathway" refers to any pathway that provides air to the targeted lung region and that is not a direct pathway. The term "direct' is used to refer to air flow that flows into or out of a targeted lung region via a direct pathway. Likewise, the term "collateral" is used to refer to fluid flow (such as air flow) that flows into or out of a targeted lung region via a collateral pathway. Thus, for example, "direct" flow is fluid flow (such as air flow) that enters or exits the targeted lung region via a direct, pathway, and "collateral" flow is fluid flow (such as air flow) that enters or exits the targeted lung region via a collateral pathway.

A collateral flow can be, for example, air flow that flows between segments of a lung, which is referred to as intralobar flow, or it can be, for example, air flow that flows between lobes of a lung, which is referred to as interlobar flow. One exemplary process of identifying a collateral pathway that provides collateral air flow into a targeted lung region is described below.

In accordance with one aspect of the disclosed methods, a targeted region of the lung is identified, wherein the targeted lung region can comprise, for example, a single one of the lung regions described above with reference to FIGS. 1-3, or the targeted lung region can comprise a collection of the regions described above. Alternately, the targeted lung region can be some other portion of the lung. The targeted lung region can be, for example, a diseased lung region for which it is desired to bronchially isolate the region for the purposes of inhibiting fluid flow into the region. As used herein, to "bronchially isolate" a lung region means to modify the flow to the targeted lung region, such as to regulate, prevent, or inhibit direct air flow to the lung region. In one embodiment, after the targeted lung region is identified, an attempt is made to bronchially isolate the targeted lung region, such as by occluding the bronchial pathway(s) that directly feed air to the targeted lung region. This may be accomplished, for example, by advancing and implanting a bronchial isolation device into the one or more bronchial pathways that directly feed air to the targeted lung region to thereby regulate direct flow into the lung region.

The bronchial isolation device can be, for example, a device that regulates the flow of air into a lung region through a bronchial passageway. Some exemplary bronchial isolation devices comprised of flow control elements are described in detail below with reference to FIGS. 19-25. In addition, the following references describe exemplary flow control elements: U.S. Pat. No. 5,954,766 entitled "Body Fluid Flow Control Device; U.S. patent application Ser. No. 09/797,910, entitled "Methods and Devices for Use in Performing Pulmonary Procedures"; and U.S. patent application Ser. No. 10/270,792, entitled "Bronchial Flow Control Devices and Methods of Use". The foregoing references are all incorporated herein by reference in their entirety and are all assigned to Emphasys Medical, Inc., the assignee of the instant application.

If the targeted lung region does not collapse, then it can be assumed that the targeted lung region is not collapsing because of collateral air flow into the lung. In such a case, it is desirable to modify collateral flow into the targeted lung region in order to encourage collapse or to achieve a desired flow dynamic for the lung region. For example, the collateral flow into the targeted lung region can be completely prevented so that there is no collateral flow into the targeted lung region. Alternately, the collateral flow into the targeted lung region can simply be reduced, such as to minimize the effect of the collateral flow on the targeted lung region.

Use of Flowable Therapeutic Agents to Reduce or Prevent Collateral Flow

One way of impeding collateral fluid flow into the targeted lung region is by injecting one or more flowable therapeutic agents into the targeted lung region in order to partially or completely seal the collateral pathway(s) that are providing collateral flow into the targeted lung region. The agent is "flowable" in that the agent is at least initially in a fluid state, which can be, for example, a liquid, gas, aerosol, etc. The agent is "therapeutic" in that, when the agent contacts lung tissue, the agent generates a reaction in the tissue of the targeted lung region that serves to reduce, inhibit, or prevent collateral fluid flow into the targeted lung region. The reaction can result in, for example (1) gluing or sealing portions of the targeted lung region together to thereby seal collateral pathways; (2) sclerosing or scarring target lung tissue to thereby occlude the collateral pathway(s) and seal off collateral flow into the targeted lung region; (3) promoting fibrosis in or around the targeted lung region to thereby seal off collateral flow into the region; (4) creating of an inflammatory response that would seal or fuse collateral pathway(s) that lead into the targeted lung region; (5) or creation of a bulking agent that fills space (such as space within the targeted lung region and/or the collateral pathway) and thereby partially or entirely seal off collateral flow into the targeted lung region.

A variety of flowable therapeutic agents have been identified that achieve one or more of the above reactions in lung tissue. The agents include, for example, the following:

(1) a foam created from either synthetic materials or natural biological materials that has one or more of the following-described properties. According to one property, the foam expands in volume from an initial injected volume to an expanded volume by a predetermined volume amount. For example, the foam may double in volume from an injected volume to expanded volume. Such volume expansion would cause the foam to fill-up and seal the volume of the targeted lung region or the volume of a collateral pathway. According to another property, the foam can be resorbable or degradable in the tissue of a patient's body, such that, when the foam is injected into the targeted lung region, the targeted lung region would absorb the foam and shrink in volume. For example, the foam could comprise a biodegradable polymer, such as polyethylene glycol (PEG) or polyglycolic acid (PGA). In another example, the foam could be a biodegradable polymer that is foamed with hydrogen or some other gas and that is permeable through the cellular structure of the foam.

When a foam as described above is injected into the targeted lung region, gas would begin to diffuse out of the foam matrix, which would cause cells within the foam to collapse. As the foam collapses, the adjacent tissue will be drawn to a smaller volume simultaneously due to adhesion between the foam and the surrounding tissue. In one embodiment, the foam has balanced properties of flow and viscosity in order to increase the likelihood that the foam will adequately fill the targeted lung region. Such balanced properties would also reduce the likelihood of the foam running or leaking into regions of the lung adjacent to the targeted lung region through the collateral pathway(s). The foam can retain a foamy consistency until it is absorbed into the lung tissue, or it can cure and harden and then dissolve over time.

(2) A sealant or glue, such as, for example, fibrin, fibrinogen and thrombin epoxy, various cyanoacrylate adhesives and sealants, such as n-butyl-2-cyanoacrylate, synthetic biocompatible sealants made from polyethylene polymers, etc.

(3) Sclerosing agents such as, for example, doxycycline, minocycline, tetracycline, bleomycin, cisplatin, doxorubicin, fluorouracil, interferon-beta, mitomycin-c, *Corynebacterium parvum*, methylprednisolone, and talc.

(4) Antibiotics such as, for example, doxycycline, minocycline or bleomycin, tetracycline, etc.

(5) Bulking agents such as, for example, collagen, gelatin, Gelfoam, or Surgicel solutions, polyvinyl acetate (PVA), ethylene vinyl alcohol copolymer (EVAL) or ethylene vinyl alcohol copolymer solutions. One example of an appropriate bulking material is the Onyx Liquid Embolic System manufactured by Micro Therapeutics, Irvine, Calif. This material is ethylene vinyl alcohol copolymer combined with micronized tantalum powder for fluoroscopy contrast dissolved in dimethl sulfoxide (DMSO) solvent. It solidifies through precipitation upon contact with an aqueous solution, such as saline, and forms a spongy mass.

(6) Agents for inducing a localized infection and scar such as, for example, a weak strain of Pneumococcus.

(7) Other agents such as mucolytics (to reduce or eliminate mucus), steroids, factor XIIIa transglutaminase.

(8) Fibrosis promoting agents such as a polypeptide growth factor (fibroblast growth factor (FGF), basic fibroblast growth factor (bFGF), transforming growth factor-beta (TGF-$\beta$)).

(9) Pro-apoptopic agents such as sphingomyelin, Bax, Bid, Bik, Bad, caspase-3, caspase-8, caspase-9, or annexin V.

(10) Components of the extracellular matrix (ECM) such as hyaluronic acid (HA), chondroitin sulfate (CS), fibronectin (Fn), or ECM-like substances such as poly-L-lysine or peptides consisting of praline and hydroxyproline.

Any well-known radiopaque contrast agent could be added to the therapeutic agent in order to facilitate viewing of the agent as it is dispersed in the targeted lung region. A sufficient quantity of agent is dispersed to seal collateral pathways, but not so much that adjacent tissue is affected. The flowable therapeutic agents that can be used to limit collateral flow into a targeted lung region are not limited to those described above.

Identification of Regions for Treatment

As discussed above, the targeted lung region can be an entire lobe of one of the lungs 110, 115, or the targeted lung region can be one or more lung segments, such as, for example, the lung segments described above with reference to FIGS. 2 and 3. In the case of the targeted lung region being a lung lobe, an attempt is made to bronchially isolate the target lobe by sealing the direct pathways(s) into the target lobe, such as by implanting a bronchial isolation device into the lobar bronchus that supplies air to the targeted lobe. If the targeted lobe still does not collapse, then it can be assumed that a collateral pathway is supplying air to the targeted lobe, wherein the collateral pathway is through an incomplete interlobar fissure. The outer surface of the lung is covered with a serous membrane called the visceral pleura. When the fissure between lobes is complete, the two adjacent lobes are separated and are completely covered with visceral pleura of all surfaces, and there is no collateral air flow possible between lobes. When the fissure is incomplete, the adjacent lobes are not completely separated, the visceral pleura does not completely surround the lobes, and parenchyma from the adjacent lobes in the incomplete portion of the fissure touch and are not separated. This incomplete formation of the fissure occurs naturally in about 50% of fissures in human lungs, and collateral air flow can occur between the lobes through these regions. See, Raasch B N, et al. Radiographic Anatomy of the Interlobar Fissure: A Study of 100 Specimens. AJR 1982;138:1043-1049. When there is collateral airflow through an incomplete interlobar fissure thereby preventing collapse of the treated lobe, the lung can be treated to cause the fissure to seal (either partially or entirely) and thereby reduce or prevent collateral flow into the targeted lung lobe via the interlobar fissure.

Figure 5:
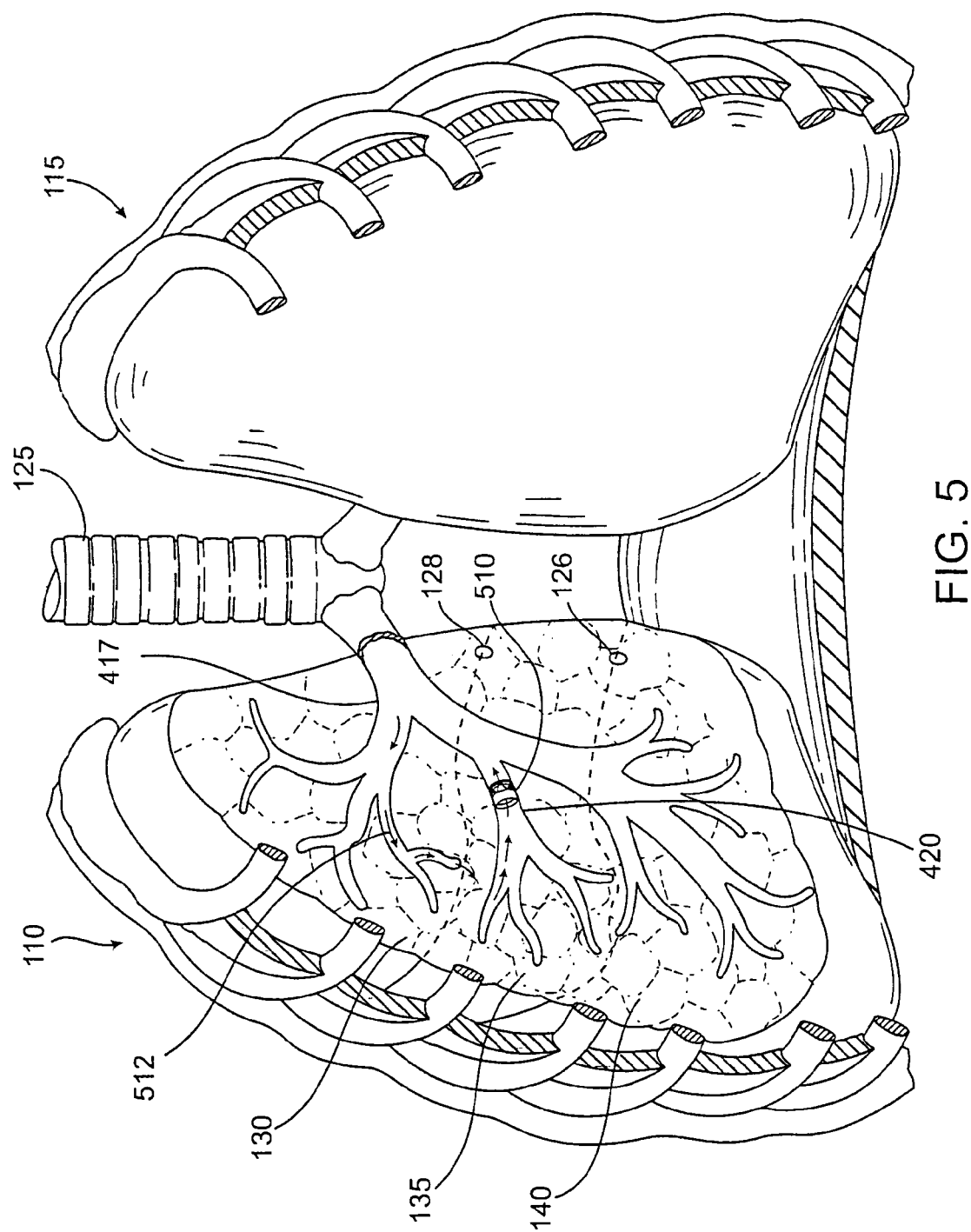
FIG. 5 illustrates an anterior view of a lung having a lung lobe that is receiving collateral air flow through a collateral pathway comprised of an incomplete interlobar fissure.

FIG. 5 shows an example of a lung lobe that has been bronchially isolated using a bronchial isolation device comprised of a flow control element, which regulates fluid flow through a bronchial passageway that supplies fluid to the lobe. The lobe receives collateral air flow through a collateral pathway comprised of an incomplete interlobar fissure. As shown in FIG. 5, a bronchial isolation device 510, such a flow control element, is implanted in the right middle lobar bronchus 420 in order to prevent direct flow into the targeted lung region comprised of the right middle lobe 135. However, the right middle lobe 135 is still receiving collateral flow (as exhibited by a series of arrows 512 in FIG. 5) through a collateral pathway comprised of an incomplete right transverse fissure 128. The collateral flow comes from the right upper lobar bronchus 417 and passes into the right middle lobe 135 through the incomplete right transverse fissure 128. Thus, the right upper lobar bronchus 417 can also be considered to be a portion of the collateral pathway into the right middle lobe 135. The collateral flow into the right middle lobe 135 could be prevented or reduced by sealing the air pathways through the incomplete right transverse fissure 128 where the middle lobe 135 contacts the inferior surface of the right upper lobe 130.

Figure 6:
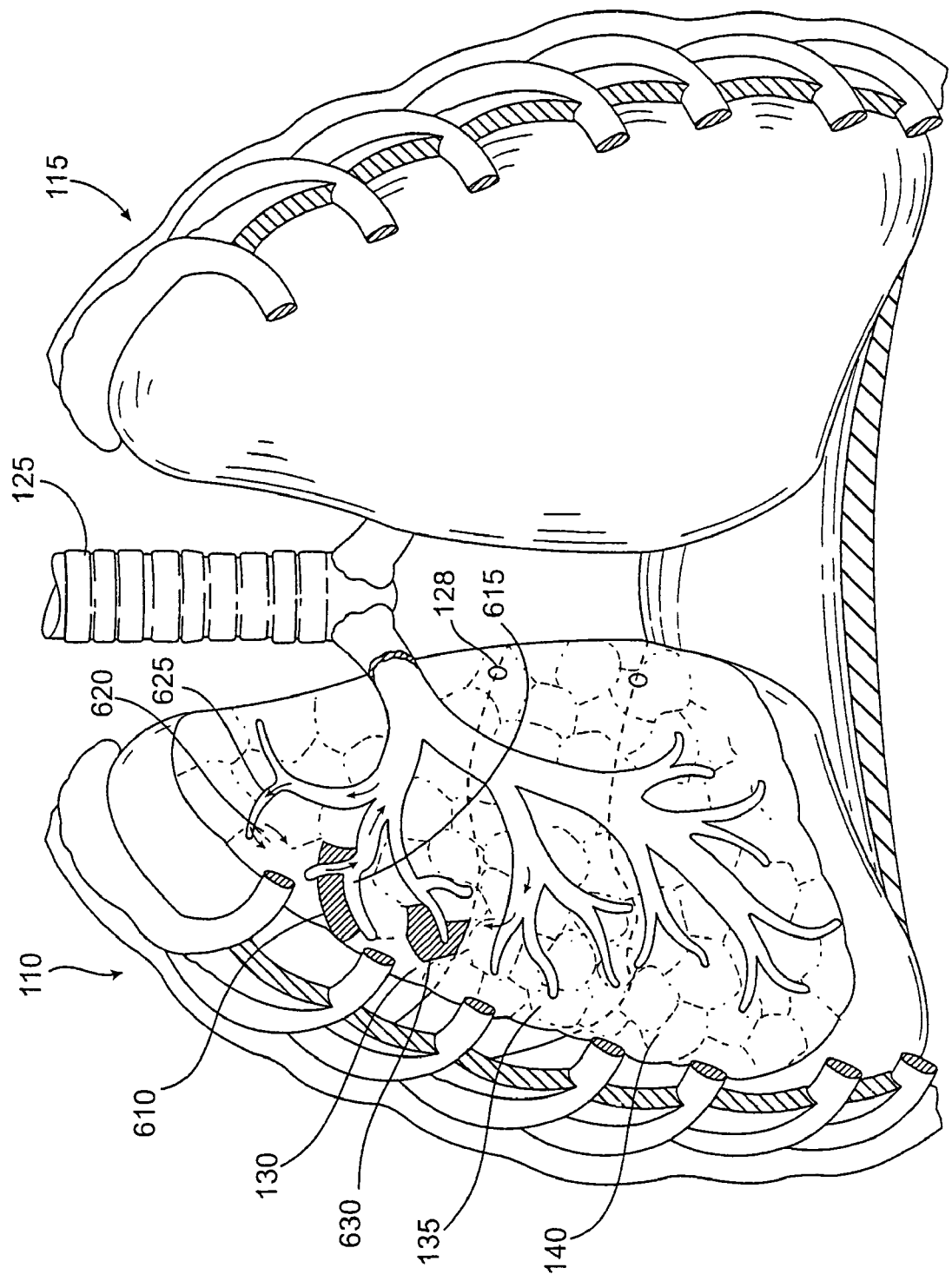
FIG. 6 illustrates an anterior view of a lung having a lung segment that is receiving collateral air flow.

In another exemplary scenario, the targeted lung region can be a specific lung segment or some other portion of the lung that is within a lobe. In this case, an attempt is made to bronchially isolate the targeted lung segment (or other portion of the lung), such as by inserting a flow control element into the direct pathway(s) to the targeted lung segment. If the targeted lung segment still does not collapse, it can be assumed that the flow is originating from other lung segments or other regions within the same lobe as the targeted segment, or from an incomplete interlobar fissure that is adjacent to the targeted lung segment. FIG. 6 shows an example of this scenario. As shown in FIG. 6, a targeted lung segment 610 is located within the right upper lobe 130. The targeted lung segment 610 can receive direct flow via segmental bronchus 615. The targeted lung segment 610 also receives collateral flow from an adjacent segment 620 that is also located within the right upper lobe 130.

In another example with reference to FIG. 6, a targeted lung segment 630 is located in the right upper lobe 130 adjacent to the right transverse fissure 128. The targeted lung segment 630 can receive collateral flow from an adjacent lung segment in the right upper lobe 130. The targeted lung segment 130 can also receive collateral flow from the right middle lobe 135 via an incomplete right transverse fissure 128, in which case a bronchial passageway of the right middle lobe 135 is the source of the collateral flow.

If collateral flow to a targeted lung segment is originating from other segments or regions within the same lobe as the targeted lung region, or is originating from a separate, adjacent lobe via an incomplete fissure, it might be necessary to determine the bronchial passageway that is supplying collateral flow to the targeted lung region. One method of determining the magnitude of collateral flow, using selective bronchial balloon catheterization combined with ventilation on a helium-based marker gas and a helium detector, is disclosed in the literature. See, Morrell N W, et al. Collateral Ventilation and Gas Exchange in Emphysema, Am J Respir Crit Care Med 1994;150:635-41.

One technique of identifying the bronchial passageway(s) that feed the parenchyma that communicates through the incomplete interlobar fissure with the targeted lung portion is now described. According to this technique, the bronchial sub-branches, such as segmental bronchi, feeding parenchyma adjacent to the interlobar fissure of an isolated lobe are determined fluoroscopically utilizing a standard guide wire. The following example illustrates the technique as applied in the right upper lobe, although the same principles could be used in any of the human lung's five lobes or any segments within those lobes. Although the lung is 3-dimensional and the airways are not sequentially related to linear lung regions (e.g., the most inferior segmental bronchus may partially feed the mid-section of a lung lobe or may preferentially feed the anterior or posterior aspect of that lobe), the goal is to determine the lowest (most inferior) sub-branch of the target upper lobe, as this sub-branch provides airflow to the lung parenchyma that borders the fissure between the upper lobe and the middle and lower lobes.

In a first step of the technique, a bronchoscope is passed through the most inferior bronchus as seen from a bronchoscopic perspective. This is performed according to well-known methods using a standard bronchoscope. A guidewire is then passed through the working channel of the bronchoscope and visually fed into the subsequent, most inferior sub-branches to the visual limits of the bronchoscope. The guidewire is then advanced further with the aid of fluoroscopic visualization. For inferior/superior determination, the fluoroscope will generally be in an anterior-posterior orientation (90 degrees to the patient's chest). The position of the guidewire relative to fluoroscopic landmarks (e.g.: relative to a rib or to the diaphragm) is then noted. The aforementioned steps are repeated in multiple sub-branches until it can be determined which bronchial sub-branch feeds the most inferior lung tissue (and thus adjacent to the interlobar fissure), and this sub-branch is selected for treatment.

Utilizing a fully articulating C-arm (fluoroscope), these steps can be repeated in other views (e.g. the camera in a 90 degree lateral view for anterior/posterior position) to map the sub-branches in 3-dimensions. In this way, a physician can determine which bronchial sub-branch or branches feed the most inferior lung tissue, tissue that borders the right middle and right lower lobes. This technique could be applied to any lobe in the lung, and to either the inferior or superior surfaces.

Delivery of Flowable Therapeutic Agent to Targeted Lung Region

The flowable therapeutic agent can be delivered to the targeted lung region according to a variety of methods. Some exemplary methods of delivering a flowable therapeutic agent to the targeted lung region are described below. Regardless of the method used, the therapeutic agent can be delivered to the targeted lung region either before or after an attempt is made to bronchially isolate the targeted lung region using a bronchial isolation device, or without bronchial isolation.

Figure 7:
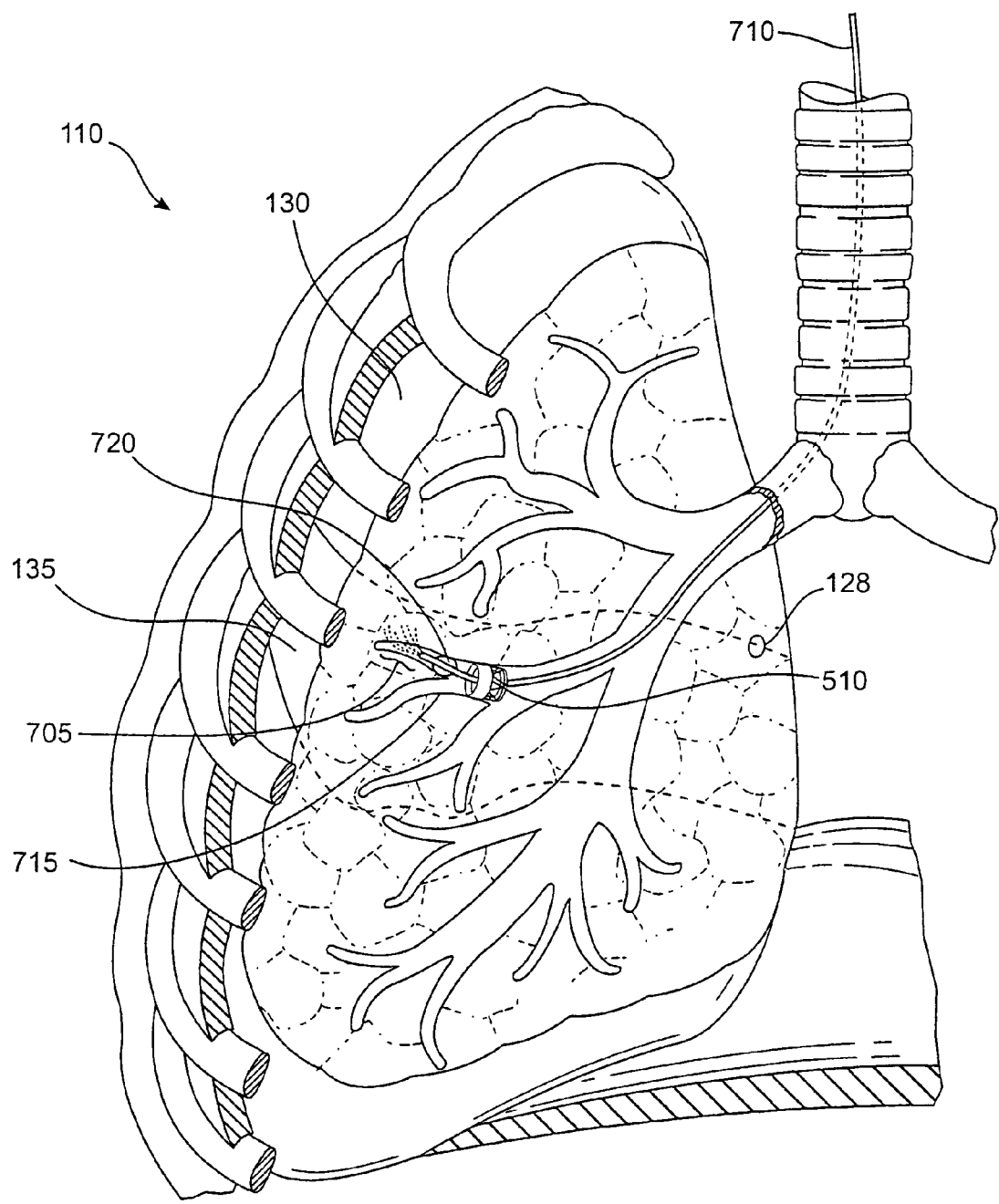
FIG. 7 illustrates the delivery of a flowable therapeutic agent to a targeted lung region using a balloon-tipped delivery catheter.

FIG. 7 illustrates an example of a method wherein a flowable therapeutic agent 705 is delivered to a targeted lung region using a delivery catheter 710. The targeted lung region is located in the right middle lobe 135 of the right lung 110. The delivery catheter 710 can be a conventional delivery catheter of the type known to those of skill in the art. The delivery catheter 710 is deployed in a bronchial passageway, such as in the segmental bronchi 715, that leads to the targeted lung region. The delivery catheter 710 is deployed such that a distal end of the catheter 710 is positioned distal of a bronchial isolation device 510 that has also been deployed in the bronchial passageway 710. As mentioned, the bronchial isolation device 510 can be deployed either before or after deployment of the delivery catheter 710.

Figure 8:
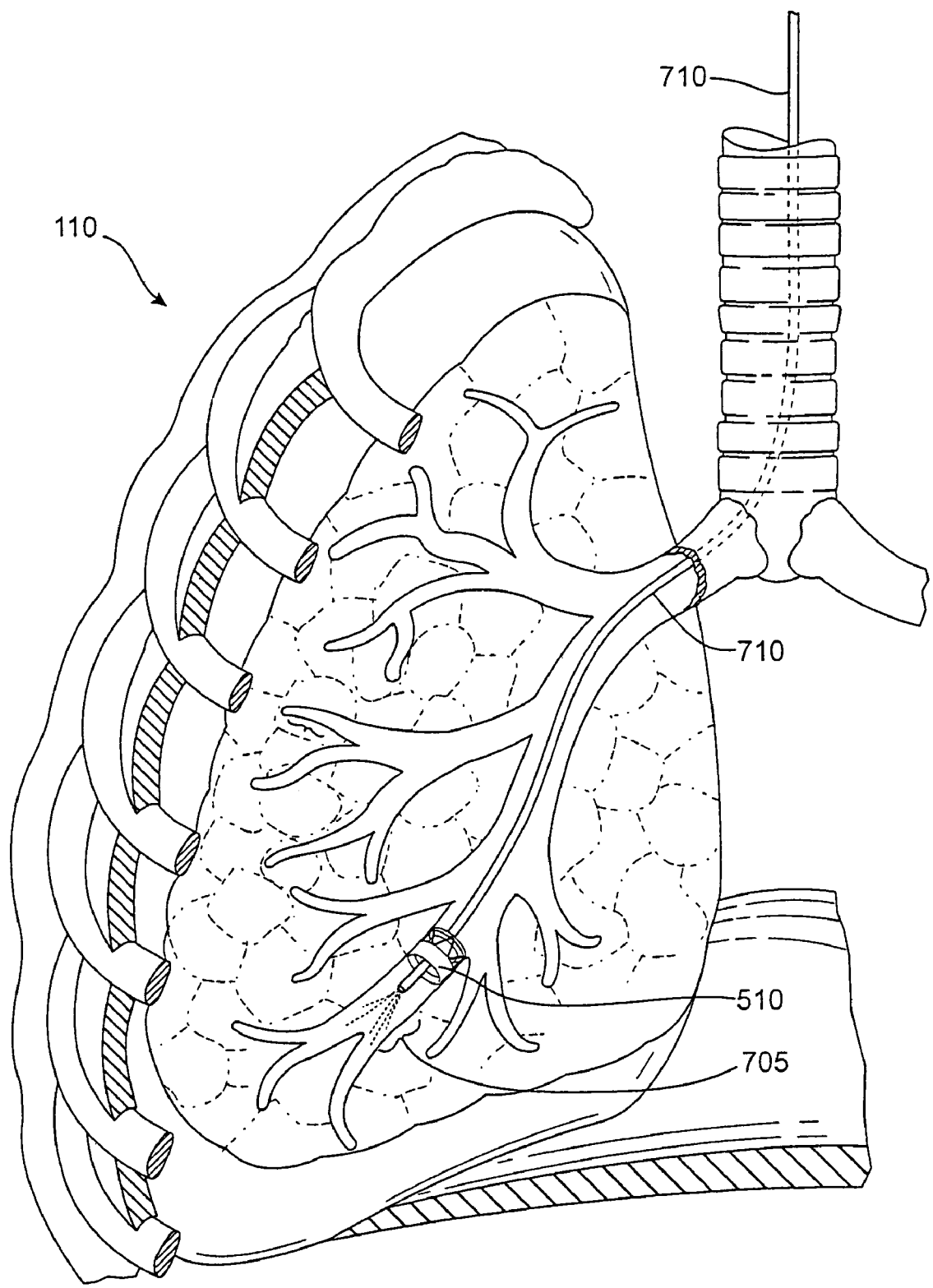
FIG. 8 illustrates the delivery of a flowable therapeutic agent to a targeted lung region using a delivery catheter.

Once the delivery catheter 710 is deployed in the targeted lung region, the flowable therapeutic agent 705 can be delivered into the targeted lung region using the delivery catheter 710. This can be accomplished by passing the flowable therapeutic agent through an internal lumen in the delivery catheter so that the agent exits a hole in the distal end of the delivery catheter 710 into the targeted lung region. As shown in FIG. 7, the distal end of the delivery catheter 710 can be sealed within the targeted lung region by inflating a balloon 720 that is disposed near the distal end of the catheter according to well-known methods. In another embodiment, shown in FIG. 8, the bronchial isolation device 510 provides the sealing so that a balloon is not needed when delivering the flowable therapeutic agent 705 using the delivery catheter 710.

Figure 9:
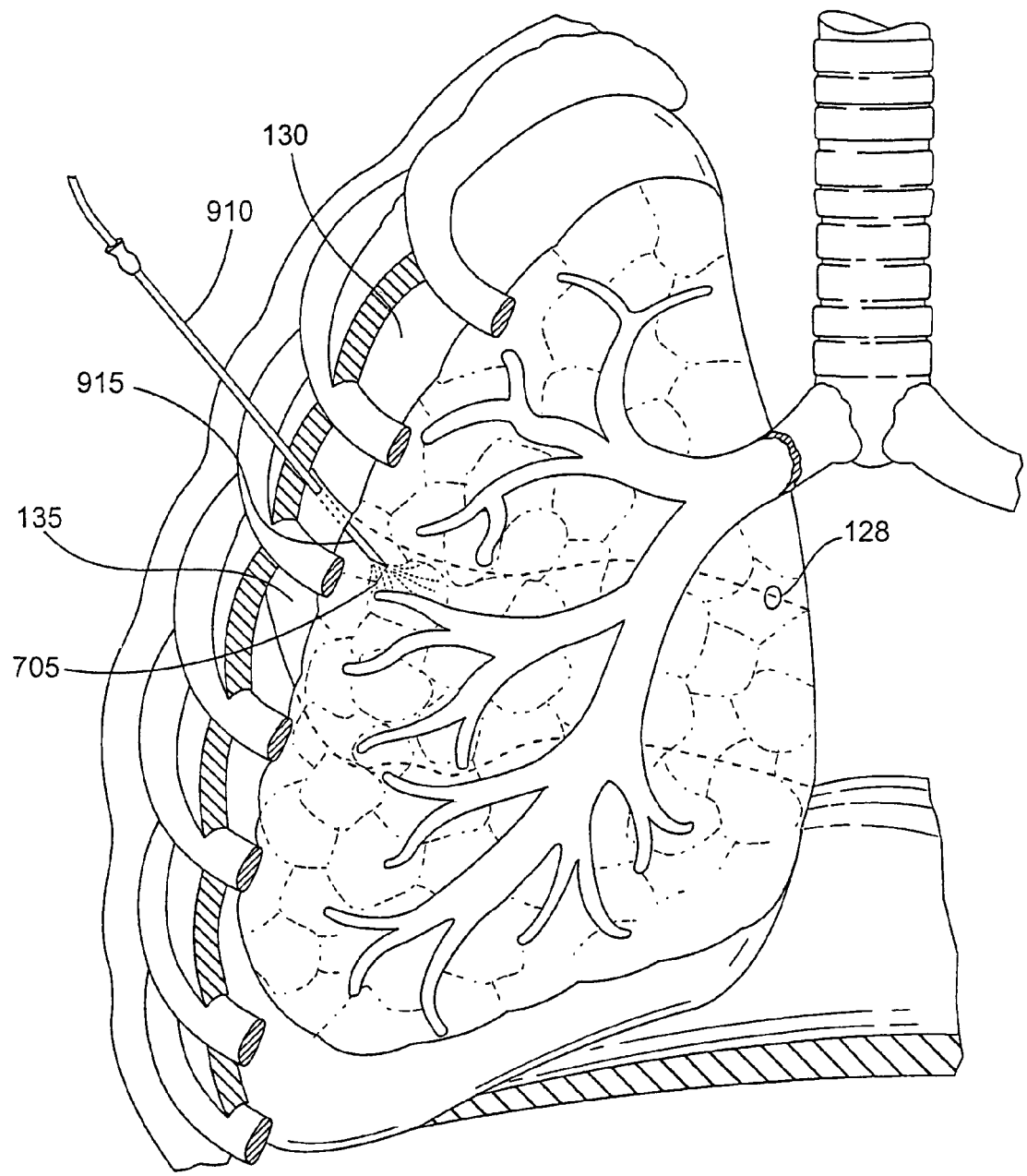
FIG. 9 illustrates the percutaneous injection of a flowable therapeutic agent to a targeted lung region.

FIG. 9 illustrates another method of delivering the flowable therapeutic agent to the targeted lung region. According to the method shown in FIG. 9, a delivery device, such as a delivery catheter or a hypodermic needle 910, is used to percutaneously inject the flowable therapeutic agent 705 directly into the lung tissue of the targeted lung region. The hypodermic needle 910 is used to puncture the chest wall according to well-known methods so that a sharpened delivery tip 915 of the needle 910 locates within the targeted lung region. For example, the targeted lung region could comprise a portion of the right middle lobe 135 located near the fissure 128, as shown in FIG. 9. The hypodermic needle 910 is then used to puncture the chest wall and the needle 910 is positioned so that the delivery tip 915 locates within the right middle lobe 135. The flowable therapeutic agent 705 is then injected directly into the targeted lung region via the hypodermic needle 910 according to well-known methods.

Figure 10:
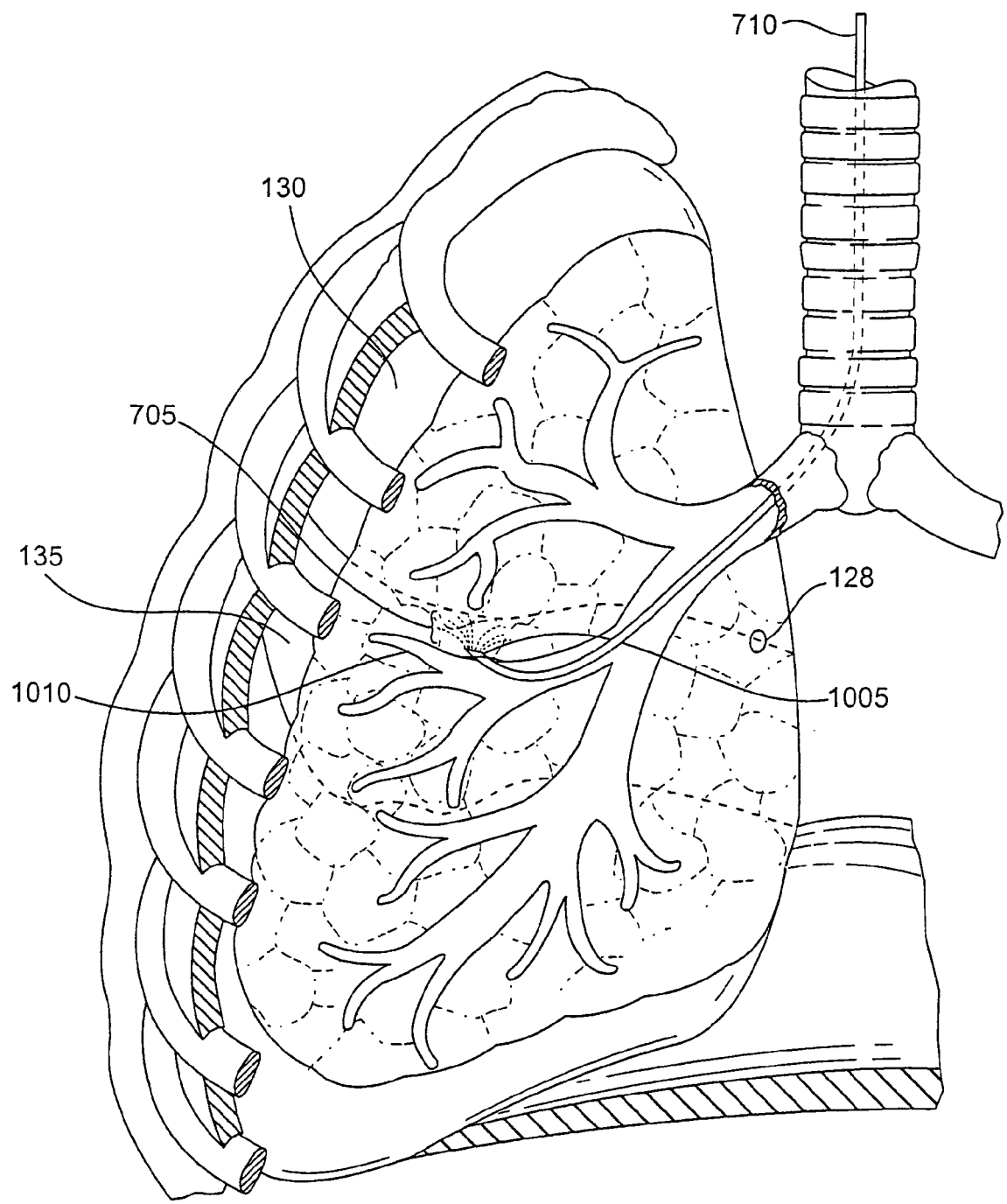
FIG. 10 illustrates the injection of a flowable therapeutic agent into a targeted lung region through a catheter that has a sharpened tip.

FIG. 10 shows yet another method of delivering the flowable therapeutic agent to the targeted lung region. According to this method, a delivery catheter 710 has a distal tip 1005 that can be used to puncture the wall of a bronchial passageway 1010 at a location that is at or near the targeted lung region. The distal tip 1005 is configured to facilitate puncturing of the bronchial wall, as described more fully below. Once the distal tip 1005 has been used to puncture the bronchial wall, the distal tip of the delivery catheter 710 is passed through the bronchial wall and the flowable therapeutic agent can be injected into the targeted lung region through the delivery catheter 710. The method shown in FIG. 10 differs from the method described above with reference to FIGS. 7 and 8 in that the method shown in FIG. 10 actually punctures the bronchial wall so that the flowable therapeutic agent can be injected directly into the lung tissue. The method shown in FIGS. 7 and 8 does not include puncturing of the bronchial wall, and the flowable therapeutic agent is injected into the bronchial lumen leading to the targeted lung region rather than directly into the lung tissue.

The puncturing of the bronchial wall can be accomplished using any of a variety of methods and devices. According to one embodiment, the distal tip 1010 of the delivery catheter is configured to facilitate puncturing of the bronchial wall. For example, the distal tip 1005 can be sharpened to an appropriate sharpness that will facilitate puncturing of a bronchial wall. It has been determined that a delivery catheter with a diameter of up to 3 millimeters (mm) will be sufficient. Alternately, a hypodermic needle can be mounted on the distal tip 1005 to facilitate puncturing of the bronchial wall. In another configuration, a stiff guidewire is delivered to the targeted lung region via the inner lumen of a flexible bronchoscope. The guidewire is then used to puncture the bronchial wall. After puncturing, a delivery catheter is delivered over the stiff guidewire to the targeted lung region. In another configuration radio frequency (RF) energy is applied to a catheter that comprises an RF cutting tip, and the cutting tip is applied to the bronchial wall at a location at or near the targeted lung region, thereby causing the bronchial wall to puncture. A device approved for this purpose is the Exhale RF Probe, Broncus Technologies, Inc. Mountain View, Calif., FDA 510 (k) #K011267. In yet another configuration, a flexible biopsy forceps is delivered through a working channel of the bronchoscope and used to cut a hole through the bronchial wall in a well-known manner.

Figure 11:
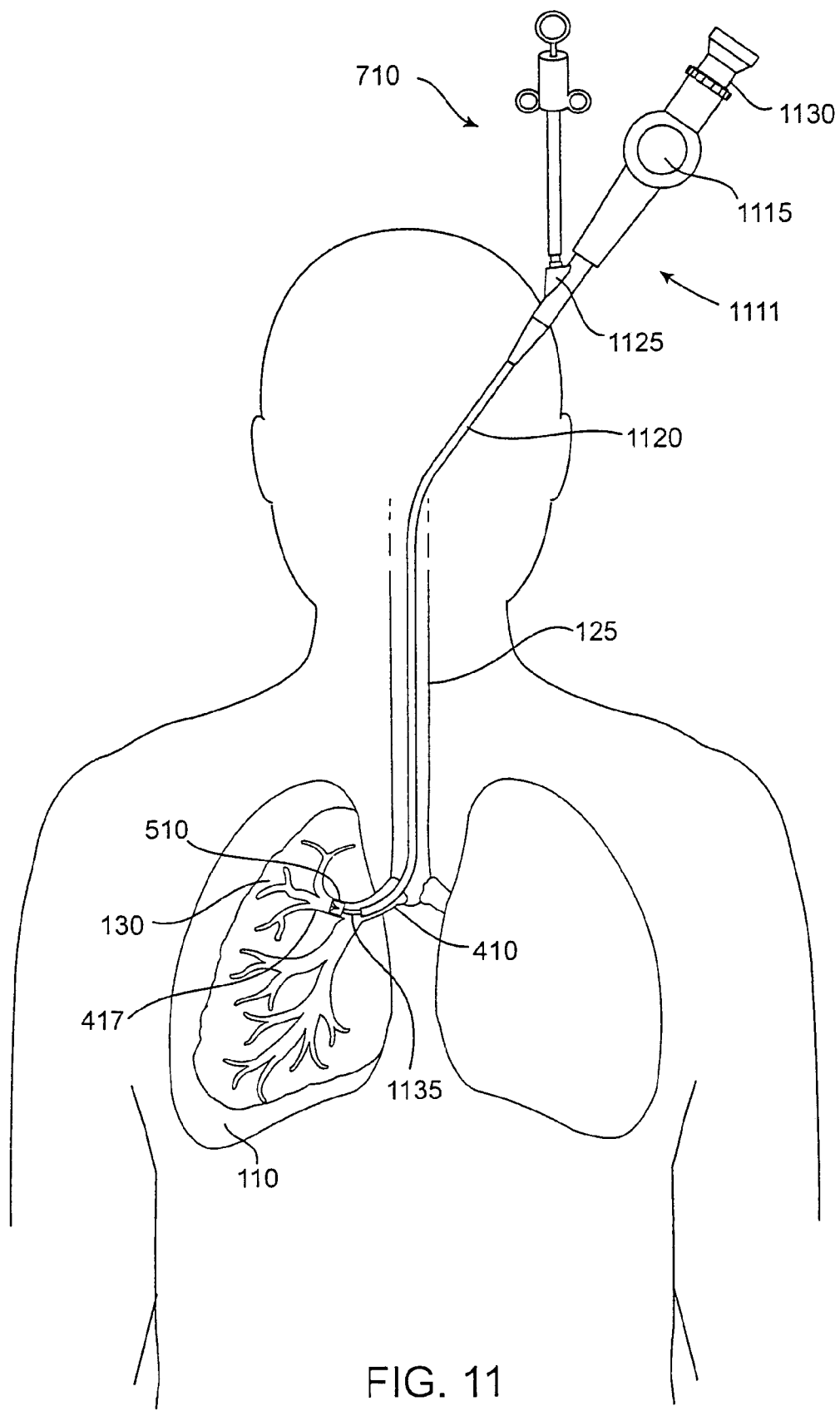
FIG. 11 illustrates the deployment of a delivery catheter in a patient using a bronchoscope.

The delivery catheter 710 can be deployed at the targeted lung region according to a variety of methods. For example, with reference to FIG. 11, the delivery catheter 710 can be deployed using a bronchoscope 1111, which in an exemplary embodiment has a steering mechanism 1115, a delivery shaft 1120, a working channel entry port 1125, and a visualization eyepiece 1130. The bronchoscope 1111 has been passed into a patient's trachea 125 and guided into the right primary bronchus 410 according to well-known methods. The delivery catheter 710 is then deployed into the working channel entry port 1125 and down a working channel (not shown) of the bronchoscope shaft 1120, and the distal end 1135 of the catheter 710 is guided to a desired location within the bronchial tree, such as to a lobar bronchi 417 located within the upper lobe 130 of the right lung 110. The steering mechanism 1115 can be used to deliver the shaft 1120 to a desired location.

Alternately, the delivery catheter 710 can have a central guidewire lumen and can be deployed using a guide wire that guides the catheter to the delivery site. The delivery catheter 710 could have a well-known steering function, which would allow the catheter 710 to be delivered with or without use of a guidewire.

In yet another method of delivering the flowable therapeutic agent, one or more nasal cannulae are deployed through a patient's nasal cavity, through the trachea, and to a desired location in the bronchial tree 120 at the targeted lung region. One or more bronchial isolation devices, such as a flow control element, can also be deployed to bronchially isolate the targeted lung region, with a distal end(s) of the cannula(e) being passed through the bronchial isolation device(s). Alternately, a catheter with multiple divided lumens or cannulae could be deployed. The cannula can be left in place for a desired amount of time and an infusion of one or more flowable therapeutic agents is deployed to the targeted lung region via the cannula. The flowable therapeutic agents could be continuously or intermittently administered at a desired flow rate until the desired level of therapeutic effect has been obtained. In another embodiment, the delivery catheter 710 can be used to bronchially isolate the targeted lung region without the use of, or in combination with the use of, a flow control element. In such a case, the distal end of the delivery catheter 710 is equipped with a balloon (such as the balloon 720 shown in FIG. 7), which is inflated to occlude or partially occlude the bronchial passageway that provides fluid flow to the targeted lung region. In this manner, fluid flow through the bronchial passageway can be reduced or eliminated.

Controlling Dispersion of the Therapeutic Agent in the Lung

In the course of delivering the therapeutic agent to the targeted lung region, it can be desirable to control the dispersion of the therapeutic agent in the lung so that the agent does not flow through any collateral pathways into areas of healthy lung tissue. It can also be desirable to move the therapeutic agent preferentially toward the collateral pathway(s) (rather than toward some other area of the lung) in order to increase the likelihood that sealing of collateral pathway(s) is successful.

Figure 12:
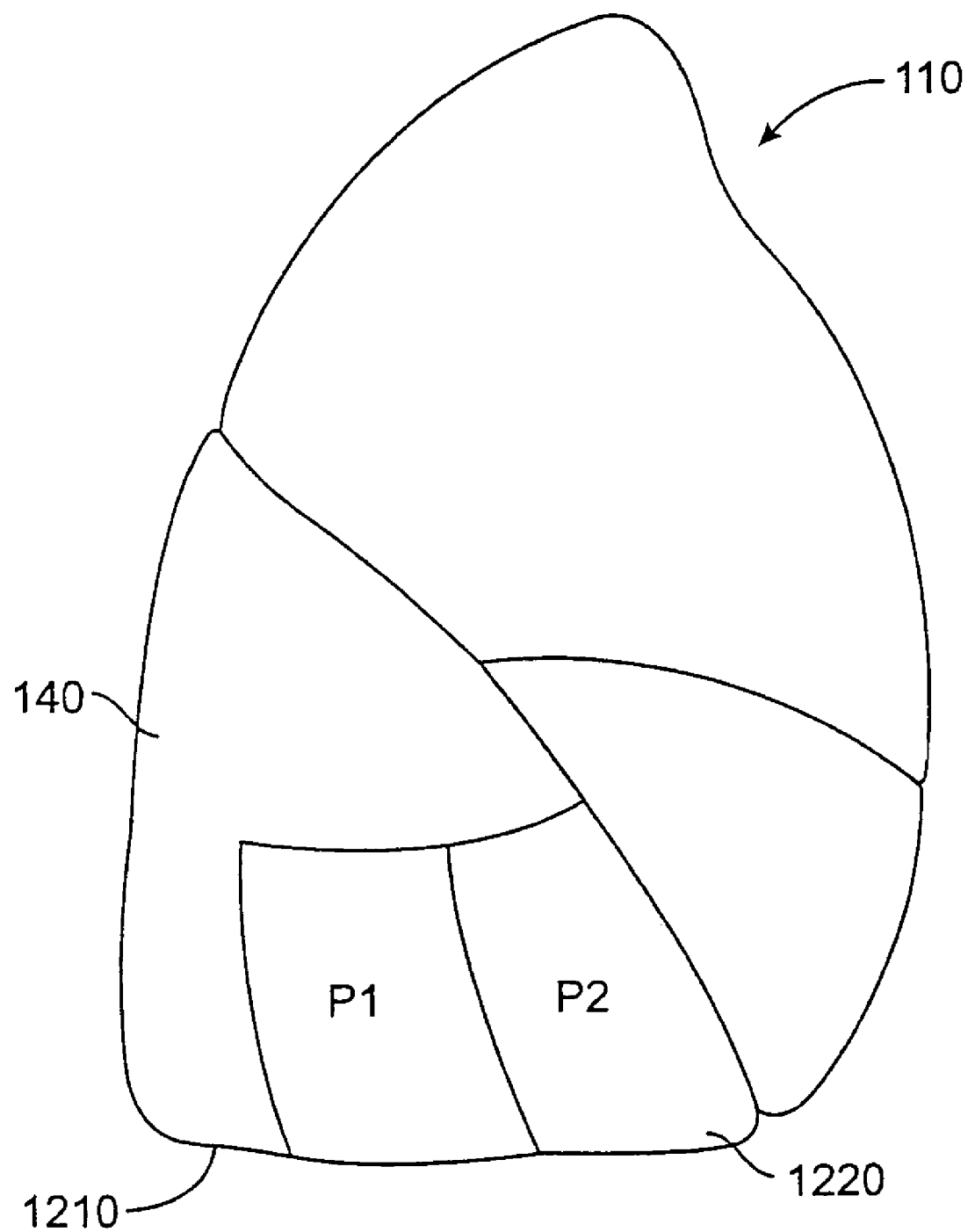
FIG. 12 illustrates a lateral view of the right lung, showing a targeted lung region and an adjacent healthy lung region.

One way of controlling the movement of the therapeutic agent within the lung is to provide pressure differentials in different regions of the lung, wherein the pressure differentials encourage the therapeutic agent to flow in a desired manner. For example, as shown in FIG. 12, a targeted lung region 1210 is located in the right lower lobe 140 of the right lung 110. A healthy lung region 1220 is located adjacent to the targeted lung region 1210. The pressure within the targeted lung region is P1 and the pressure within the adjacent lung region 1220 is P2. If P1 is greater than P2, then a therapeutic agent located in the targeted lung region 1210 will be inclined to flow toward the adjacent lung region 1220 due to the pressure differential. Likewise, if P2 is greater P1, then a therapeutic agent located in the targeted lung region 1210 will be inclined to flow away from the adjacent lung region 1220.

One way to accomplish such a pressure differential is to control the injection pressure that is used to inject the therapeutic agent into the targeted lung region, and to also control a back pressure in an adjacent lung region where collateral pathways to the targeted lung region originate. If the therapeutic agent is radiopaque, a physician can view the extent of the therapeutic agent dispersion while also varying the injection pressure and the back pressure to control the dispersion.

Figure 13:
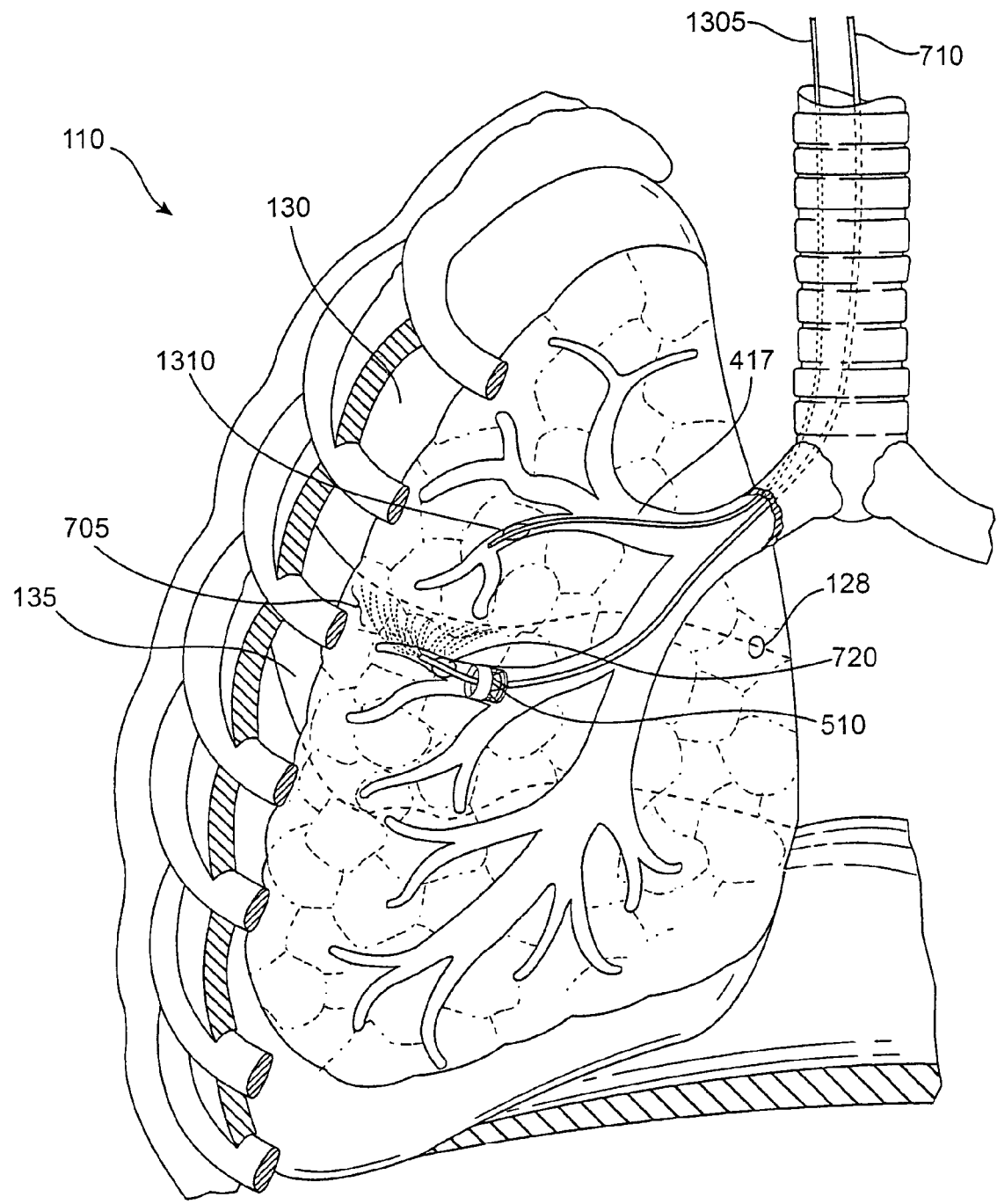
FIG. 13 illustrates the injection of a therapeutic agent into a targeted lung region, controlled by applied pressure in an adjacent lung region.

This is described in more detail with reference to FIG. 13, which shows a cross-sectional view of the right lung 110, wherein the targeted lung region comprises the right middle lobe 135, which is adjacent to a healthier lung region comprised of the right upper lobe 130. The incomplete right transverse fissure 128 provides a collateral pathway through which collateral flow originating in the right upper lobe 130 passes into the right middle lobe 135. A first delivery catheter 710, which can have a balloon 720, is passed through a bronchial isolation device 510 so that the distal end of the catheter 710 is disposed in the targeted lung region. A second catheter 1305 is deployed in a bronchial passageway that provides flow to a lung region adjacent to the target region, wherein some collateral flow originates at the adjacent lung region. For example, FIG. 13 shows the second catheter 1305 deployed through the right lobar bronchus 417, which provides flow to the right upper lobe 130 where the collateral flow into the right middle lobe originates. The second catheter can have a balloon 1310 that is inflated.

The delivery catheter 710 is then used to inject the flowable therapeutic agent 705 into the targeted lung region at a desired injection pressure. This will cause the targeted lung region to achieve a pressure P1. While the therapeutic agent is being injected, a suction can be applied to the distal end of the second catheter 1305 to thereby achieve a pressure P2 in the adjacent lung region comprised of the right upper lobe 130. By controlling the injection pressure and suction, a desired pressure differential between P1 and P2 can be achieved to thereby control the dispersion of the therapeutic agent. The pressure differential can be manipulated to encourage the therapeutic agent to flow toward the collateral pathway and even enter the collateral pathway. As discussed, the dispersion can be visually monitored if the therapeutic agent includes a radiopaque.

When the desired dispersion level has been achieved, such as when the therapeutic agent has filled the targeted lung region or has filled the collateral pathways, it might then be desirable to further control the dispersion to reduce the likelihood that the therapeutic agent will flow into the healthy lung region. This can be accomplished by again varying the pressure differential so that the therapeutic agent no longer flows towards the healthy lung region. For example, the injection pressure can be reduced or eliminated, while also changing the suction pressure at the second catheter 1305. Suction can then be applied to the delivery catheter 710 to remove any excess therapeutic agent from the targeted lung region. The catheters 710, 1305 are then removed. In this manner, the therapeutic agent is preferentially moved toward the collateral pathway(s).

The aforementioned technique for sealing the collateral flow pathway could also be performed prior to the implantation of the bronchial isolation device(s) 510.

Follow-On Therapy After Treatment with Flowable Therapeutic Agent

After the infusion of the flowable therapeutic agents into the targeted lung region, a follow-on therapy procedure can be followed. According to one procedure, the treated portion of the lung (the portion of the lung to which the therapeutic agent was applied) is left alone, with the therapeutic agent in place. The treated lung portion is allowed to collapse by either absorption of the therapeutic agent by the body, absorption of the trapped gas in the isolated lung region, exhalation of trapped gas out through a flow control device (such as an implanted one-way or two-way valve device) or any combination of these events.

According to another follow-on therapy procedure, the therapeutic agent is removed from the lung following the passage of a predetermined treatment period. The therapeutic agent could be removed after a short period of time such as one or two minutes, or a longer period of 30 or 60 minutes. Alternatively, if required, the therapeutic agent could be removed in a separate procedure hours or days later. The necessary time period would depend on the particular therapeutic agent used. This could be done with the implanted bronchial isolation devices in place, or could be done before implantation of the bronchial isolation devices if the therapeutic agent was deployed prior to implantation of the bronchial isolation devices. The therapeutic agent can be removed from the lung in any number of ways, which include the following:

(a) Inflating a balloon catheter in the bronchial passageway leading to the targeted lung region and aspirating through the catheter central lumen. If bronchial isolation devices had been implanted already, the suction in the catheter would pull the excess therapeutic agent through the one-way or two-way valves of the isolation devices. This method is likely not used where the implanted devices are plugs or occluders.

(b) Crossing the implanted one-way or two-way valves with a catheter and applying suction through the central lumen of the catheter. The catheter could either be sealed by the valve in the implanted device, or it could be a balloon catheter where the balloon is inflated in the bronchial passageway distal to the implanted device.

(c) Percutaneously suctioning the therapeutic agent directly out of the lung tissue, such as by using a hypodermic needle.

(d) Suctioning the therapeutic agent out of the targeted lung region through the a hole created in the bronchial wall. This can be done using a new catheter or using the same catheter as was used to inject the agent.

Thus, there have been disclosed several basic approaches to injecting a flowable therapeutic agent for preventing or reducing collateral flow into a targeted lung region. Some examples of the basic approaches are summarized as follows:

(a) Implant one or more bronchial isolation devices to isolate targeted lung region; inject a flowable therapeutic agent into the targeted lung region distal to the bronchial isolation devices; allow the lung region to collapse, such as, for example, by absorption of the therapeutic agent by the body, absorption of the trapped gas in the isolated lung portion, exhalation of trapped gas out through the implanted one-way or two-way valve devices, or any combination of these events.

(b) Implant one or more bronchial isolation devices; inject a flowable therapeutic agent into the targeted lung region distal to devices; wait a pre-determined treatment time period; remove the therapeutic agent, such as, for example, by using suction, needle aspiration, etc.; and allow the lung region to collapse, such as, for example, by absorption of the trapped gas in the isolated lung portion, exhalation of trapped gas out through the implanted one-way or two-way valve devices, or both.

(c) Inject a flowable therapeutic agent into the targeted lung region; implant bronchial isolation devices; allow the targeted lung region to collapse, such as, for example, by absorption of the therapeutic agent by the body, absorption of the trapped gas in the isolated lung portion, exhalation of trapped gas out through the implanted one-way or two-way valve devices, or any combination of these events.

(d) Inject a flowable a therapeutic agent into parenchyma of the targeted lung region; implant one or more bronchial isolation devices; wait a pre-determined treatment time period; remove the therapeutic agent, such as, for example, using suction, needle aspiration, etc.; and allow lung region to collapse, such as, for example, by absorption of the trapped gas in the isolated lung portion, exhalation of trapped gas out through the implanted one-way or two-way valve devices, or both.

(e) Inject a flowable therapeutic agent into the targeted lung region; wait a pre-determined treatment time period; remove therapeutic agent; implant bronchial isolation devices; and allow the lung region to collapse.

(f) Temporarily isolate the targeted lung region; inject a flowable therapeutic agent into the targeted lung region; wait a pre-determined treatment time period; and remove therapeutic agent.

(g) Temporarily isolate the targeted lung region; and inject a flowable therapeutic agent into the targeted lung region.

Application of Energy to Reduce or Prevent Collateral Flow

An alternate way of reducing or preventing collateral fluid flow into the targeted lung region is to apply energy to the targeted lung region, wherein the application of energy generates a reaction in the tissue of the targeted lung region that serves to reduce or prevent collateral fluid flow into the targeted lung region. The reaction can result in, for example: (1) gluing or sealing portions of the lung together to thereby partially or entirely seal collateral pathways; (2) sclerosing or scarring target lung tissue to thereby partially or entirely occlude the collateral pathway(s) and partially or entirely seal off collateral flow into the targeted lung region; (3) promoting fibrosis in or around the targeted lung region to thereby partially or entirely seal off collateral flow into the region; (4) creating of an inflammatory response that would partially or entirely seal or fuse collateral pathway(s) that lead into the targeted lung region. A variety of energy sources have been identified that can be used to apply energy to lung tissue to achieve any of the aforementioned reactions. The types of energy include Beta-emitting radiation, radio frequency energy, heat, ultrasound, cryo-ablation, laser energy, and electrical energy. The process of identifying the lung region for treatment can be the same as that described above with reference to the use of the flowable therapeutic agent.

A variety of different methods can be used to deliver energy to a desired location in the targeted lung region. Regardless of the method used, the therapeutic agent can be delivered to the targeted lung region either without bronchial isolation, or before or after an attempt is made to bronchially isolate the targeted lung region using a bronchial isolation device.

Figure 14:
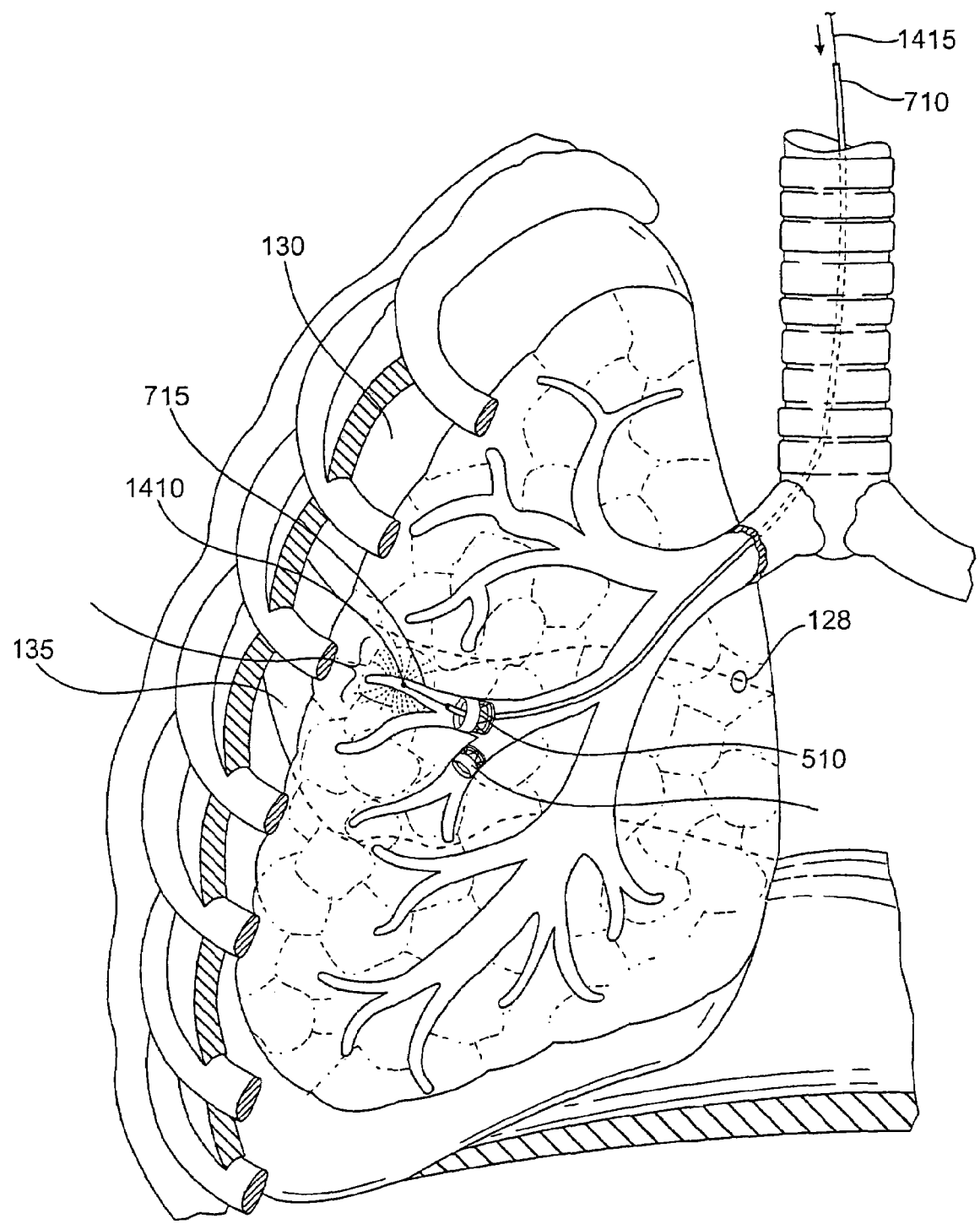
FIG. 14 illustrates the treatment of collateral flow paths using a beta-emitting radiation source.

FIG. 14 illustrates a method wherein an energy source is delivered to a targeted lung region using a delivery catheter 710. The targeted lung region is located in the right middle lobe 135 of the right lung 110. The delivery catheter 710 can be a conventional delivery catheter of the type known to those of skill in the art. The delivery catheter 710 is deployed in a bronchial passageway, such as in the sub-segmental bronchi 715, that leads to the targeted lung region. A distal end of the catheter 710 is inserted into the bronchial passageway and is positioned distal of a bronchial isolation device 510 that has been deployed in a bronchial passageway that provides direct flow to the targeted lung region. As discussed above, the bronchial isolation device 510 can be deployed either before or after deployment of the delivery catheter 710.

Once the delivery catheter 710 is deployed in the targeted lung region, an energy source 1410 can be delivered into the targeted lung region using the delivery catheter 710. This can be accomplished, for example, by passing a push wire 1415 having a distally-mounted energy source 1410 through an internal lumen in the delivery catheter 710 so that the energy source 1410 exits a hole in the distal end of the delivery catheter 710 into the targeted lung region. Alternately, the energy source 1410 can be mounted on the distal end of the delivery catheter 710. The distal end of the delivery catheter 710 can be sealed within the targeted lung region by inflating a balloon that is disposed near the distal end of the catheter according to well-known methods. Alternately, the bronchial isolation device 510 can provide the sealing so that a balloon is not needed.

According to another method of delivering the energy, a delivery device, such as delivery catheter or a hypodermic needle, is used to percutaneously reach the targeted lung region by puncturing the chest wall and outer surface of the lung. The energy source is then advanced directly into the lung tissue. This would be similar to the method shown in FIG. 9, although an energy source would be used in place of the flowable therapeutic agent.

In yet another method of delivering the energy to the targeted lung region, a delivery catheter has a distal tip that can be used to puncture the wall of a bronchial passageway that is located at or near the targeted lung region. The distal tip is configured to facilitate puncturing of the bronchial wall. Once the distal tip has been used to puncture the bronchial wall, the energy source is advanced into the targeted lung region through the delivery catheter. This would be similar to the process shown in FIG. 10. The puncturing of the bronchial wall can be accomplished using any of a variety of methods and devices, such as was described above with reference to FIG. 10.

The delivery catheter for delivering the energy source to the targeted lung region could be deployed in the same manner described above with reference to the flowable therapeutic agents, such as by using a bronchoscope.

Exemplary Method for Applying Energy to Targeted Lung Region

The delivery of beta-emitting radiation could be accomplished with a brachytherapy delivery system that includes a beta-emitting radiation source mounted to the end of a delivery catheter, such as was described above. As mentioned previously, this could be done either before or after the implantation of bronchial isolation devices.

According to one method of applying the energy, a beta radiation-emitting source is passed through one or more target bronchial passageways, either sequentially or concurrently, that lead to the targeted lung region. The source can also be passed through one or more of the bronchial isolation devices that were previously implanted. The radiation source is left in place for a period of time so as to elicit a scarring/healing response in the treated lung tissue. For example, it may be discovered through animal and/or human clinical trials that an exposure time period of 30 minutes to one hour will achieve satisfactory results. A maximum time may be identified wherein the risk of radiation to the surrounding tissue is greater than the benefits of scarring the target tissue. For example, it may be discovered that the radiation source can remain in up to an hour, but that exposure for greater than 90 minutes increases risk to the patient.

In another application method, the application procedure is performed over a predetermined time period and/or over bronchial sub-branches. For example, a patient can first be admitted for a procedure to deploy bronchial isolation devices, such as flow limiting valves, and then discharged with periodic reassessment of anatomical or clinical results. The physician and patient could decide when the next step of transvalvular brachytherapy should take place (e.g.: 15-30 days after the primary procedure). Brachytherapy could also be staged over time in such a way as to minimize risk while continually assessing benefit (e.g.: valves placed day one, first brachytherapy procedure of 30 minutes exposure day 30, second brachytherapy procedure of 30 minutes at day 60, etc.). The first brachytherapy session could be targeted at the RUL, inferior sub-segment of the anterior, segmental bronchus; the second session would target the RUL superior sub-segment of the anterior, segmental bronchus; etc.

The same procedures described above for beta-emitting radiation could be followed for other radiation sources such as RF energy, heat, ultrasound, or cryo-ablation. These energy sources might require different treatment times, a different number of treatment sites, etc., but the general application method would be the same.

Use of Flow-Limiting Isolation Devices to Limit Collateral Flow

Another way of impeding collateral fluid flow into the targeted lung region is now described, wherein flow-limiting devices are implanted in the bronchial passageway leading to lung regions adjacent to the target region, wherein the adjacent lung region that is not targeted for collapse.

As with the previously described methods, the lung region targeted for isolation and collapse is identified, and bronchial isolation devices are implanted in all airways that provide direct flow to the targeted lung region. The implanted isolation devices can be, for example, one-way valves that allow flow in the exhalation direction only, one-way valves that allow flow in the inhalation direction only, occluders or plugs that prevent flow in either direction, or two-way valves that control flow in both directions according to well-known methods. If the lung region does not collapse, such as due to either absorption atelectasis, or through exhalation of trapped gas through the implanted devices, then the lung region is likely being kept inflated through collateral in-flow through collateral pathways from adjacent lung regions. If the collateral flow from the adjacent lung regions could be reduced substantially or eliminated, the targeted lung region will likely collapse.

One way to reduce or substantially eliminate the collateral flow from adjacent lung regions is to implant inhalation flow limiting two-way valve devices in the bronchial passageways leading to adjacent lung regions not targeted for collapse, wherein the adjacent lung regions act as a source for collateral flow into the targeted lung region. Such devices would allow free fluid flow in the exhalation direction for the adjacent lung regions, but would limit the flow to a predetermined level in the inhalation direction. As a result, flow into the adjacent lung region would be limited, thereby limiting the flow of gas into the targeted lung region through the collateral pathways from the adjacent lung regions. The flow limitation is desirably sufficient to allow the isolated lung region to collapse, but would not collapse the adjacent lung regions. Once sufficient time had passed to allow the targeted lung region to become chronically atelectatic, the flow limiting two-way valve devices could be removed from the adjacent lung regions in order to restore normal ventilation to the lung portion not targeted for collapse.

Figure 15:
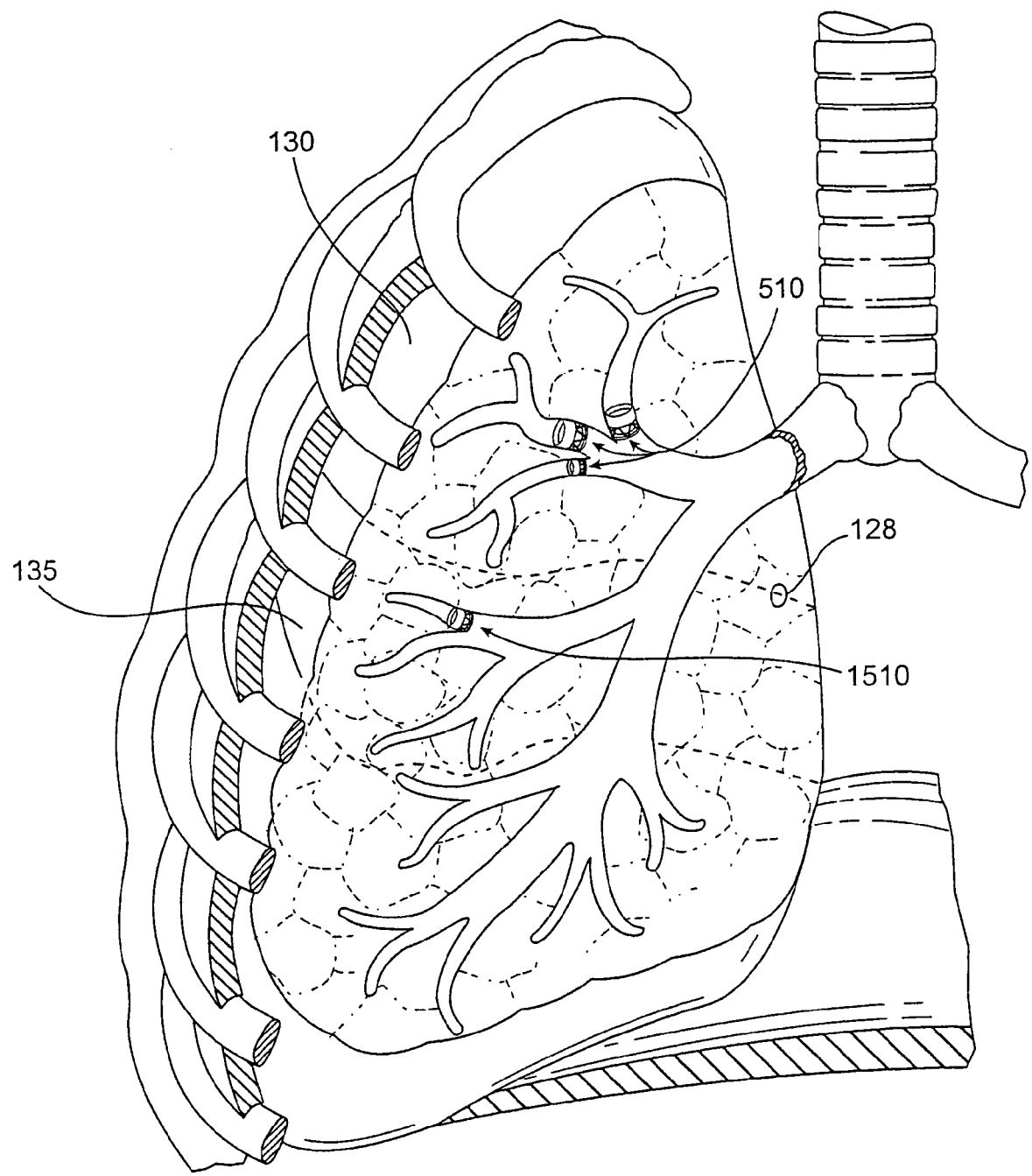
FIG. 15 illustrates the treatment of collateral flow paths using flow-limiting isolation devices.

An example of this method is shown in FIG. 15, which shows a targeted lung region comprised of the right upper lobe 130 that is isolated by one-way bronchial isolation devices 510 that are implanted in all bronchial passageways leading to the lobe 130. The devices 510 are one-way valve devices that stop all flow in the inhalation direction to thereby prevent direct flow into the lobe 130. A flow limiting two-way valve bronchial isolation device 1510 is implanted in the bronchial passageway in the right middle lobe 135 in the segment that lies just below the interlobar fissure 28 adjacent to the lobe 130. The device 1510 allows free flow in the exhalation direction and a limited flow in the inhalation direction. This limits the flow into the middle lobe 135, in a manner determined by the back flow restriction of the two-way valve. By limiting the flow into the middle lobe 135, the collateral flow into the targeted upper lobe 130 that originates in the middle lobe 130 is also limited. The flow limitation into the middle lobe 135 is sufficient to allow the right upper lobe 130 to collapse, as the collateral flow into the upper lobe 135 via the fissure 28 is insufficient to inflate the upper lobe 130.

One exemplary embodiment of a flow limiting two-way valve 2500 is shown in FIGS. 22-25. In this embodiment, the valve would behave as a one-way valve in the forward or exhalation direction in that it would allow free flow of fluid through the valve. However, the valve would also allow a controlled rate of flow in the reverse or inhalation direction. This could be achieved in a duckbill style valve by adding a small flow channel 2510 through the lips 2512 of the valve, as shown in FIG. 25. The reverse flow channel shown would allow fluid to flow in the inhalation direction, and the rate of flow would be controlled by diameter and length of the flow channel.

Use of Percutaneous Suction to Limit Collateral Flow

Another method for limiting collateral flow into a targeted lung region is through the use of percutaneous suction. As discussed, bronchial isolation devices may be implanted in any bronchial passageways that provide direct flow to the targeted lung region. Percutaneous suction is then applied to the targeted lung region for a time period sufficient to adhere or fuse the lung tissue in the targeted lung region in a collapsed state such that the targeted lung region will not re-inflate through collateral pathways after the suction is stopped.

The percutaneous suction method is described in more detail with reference to FIG. 16, which shows the targeted lung region being located in the right upper lobe 130. An attempt is made to bronchially isolate the targeted lung region by implanting one or more bronchial isolation devices 705 in bronchial passageway that provide direct flow into the targeted lung region. A suction catheter 1610 is percutaneously inserted into the targeted lung region, such as by inserting the catheter 705 through the rib space in a well-known manner. The suction catheter 1610 includes an internal lumen and has a distal end 1615 on which are located one or more suction holes 1620 that communicate with the internal lumen. A suction force can be applied to a proximal end 1625 of the catheter 1610 to suck fluid into the internal lumen through the suction holes 1620 on the distal end 1615 of the catheter 1610. A fixation balloon 1630 is mounted on the catheter 1610 a short distance from the distal end 1615 of the catheter 1610. In one embodiment, the fixation balloon 1630 is mounted approximately 2 centimeters from the distal end 1615. An exemplary suction catheter that can be used is the 8-French Venography Catheter, manufactured by The Cook Group, Inc., Bloomington, Ind.

Figure 16:
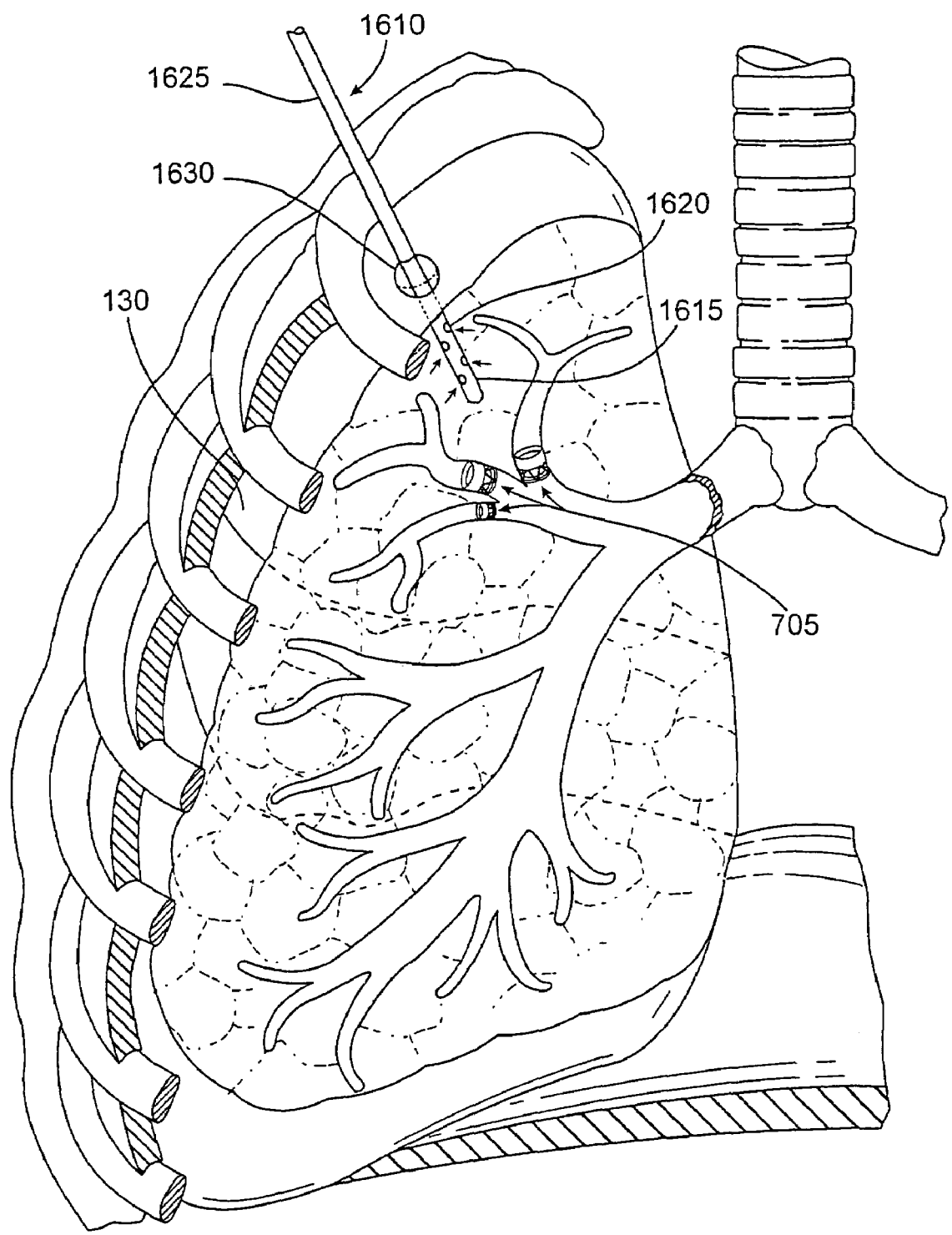
FIG. 16 illustrates the percutaneous suction of a targeted lung region using a suction catheter.

As shown in FIG. 16, the suction catheter 1610 is percutaneously inserted into the targeted lung region so that the suction holes 1620 in the distal end 1615 are positioned within the targeted lung region. The fixation balloon 1630 is positioned in the pleural space of the lung and is then inflated to thereby fix the suction catheter 1610 in a fixed position and to also seal the incision that was used to percutaneously insert the catheter 1610. The suction catheter 1610 can be maneuvered into the correct location using guidance assistance, such as computer tomography (CT) or fluoroscopic guidance.

After the suction catheter 1610 has been properly positioned, a suction force can be applied to the internal lumen of the catheter to thereby cause a sucking force that draws fluid into the internal lumen through the suction holes 1620. The suction force will draw air or other fluid in the targeted lung region into the internal lumen through the suction holes 1620, which will aspirate the targeted lung region into a collapsed state. It has been determined that a suction force of approximately 100-160 mmHg is sufficient to aspirate the targeted lung region into a collapsed state. The suction force can be continuously maintained for a time period sufficient to permanently collapse the lung and reduce the likelihood of inflation through collateral pathways. In one embodiment, the suction is continuously maintained for a minimum time period of eight hours. In another embodiment, the suction is maintained for a time period of one to eight days. The suction can be performed while the patient is on bed rest, using a stationary vacuum source, or it could be performed using a portable vacuum source in order to permit the patient to ambulate.

After the suction time period has elapsed, a flowable therapeutic agent (such as any of the agents described above) can optionally be infused into the targeted lung region. This could be performed using the suction catheter 1610, such as by infusing the agent through a separate internal lumen located in the catheter 1610 or through the same lumen that was used for suction. The therapeutic agent could be used to increase the likelihood that the targeted lung region is properly sealed. The fixation balloon 1630 is then deflated and the suction catheter 1610 is removed.

Use of Two-Part Adhesive to Limit Collateral Flow

According to another method of inhibiting collateral flow into a targeted lung region, a two-part adhesive or glue is used to occlude a collateral pathway to the targeted lung region. The adhesive can comprise a two-part mixture that includes a first part and a second part, wherein the first part and the second part collectively solidify when brought into contact with each other. The two parts do not necessarily require complete mixing in order for the solidification to occur. The solidification can be triggered, for example, by a catalytic reaction that occurs when the two parts contact one another. In one embodiment, the two-part glue is a fibrin glue and the two parts of the glue are thrombin and fibrinogen.

Figure 17:
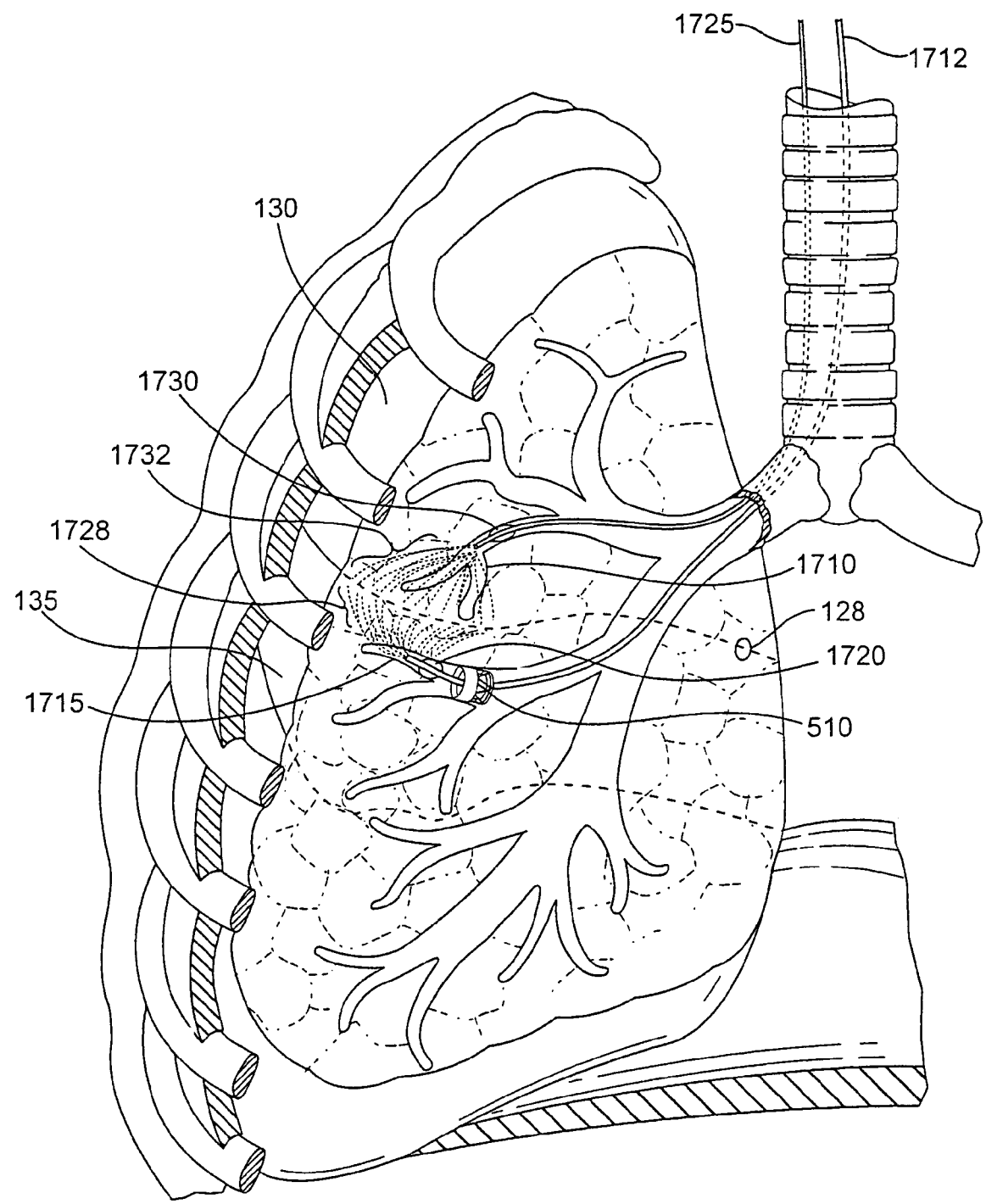
FIG. 17 illustrates the sealing of collateral flow paths between the right upper lobe and the right middle lobe through the use of a two-part adhesive.

A method for deploying a two-part adhesive in order to seal a collateral pathway is now described. The collateral pathway is located in a lung region between two or more bronchial passageways, such as a first bronchial passageway and a second bronchial passageway. For example, as shown in FIG. 17, the collateral pathway can be an incomplete interlobar fissure 28 that is located between a first bronchial passageway 1710 and a second bronchial passageway 1715. The bronchial passageway are not necessarily in the same lobe. For example, in FIG. 17 the bronchial passageway 1710 is in the right upper lobe 130 and the bronchial passageway 1715 is in the right middle lobe 135, where the targeted lung region is also located.

According to the method, the first part of the two-part adhesive is injected into the first bronchial passageway and the second part of the two-part adhesive is injected into the second bronchial passageway. The injection pressure and flow rates of the first and second parts can be controlled to encourage the first and second parts to flow to a common location, wherein the common location coincides with the location of the collateral flow path. That is, the first and second parts will contact one another within the collateral flow path. As mentioned, the first and second parts solidify when they contact one another. In this manner, the first and second parts solidify within the collateral flow path and thereby partially or entirely seal the collateral flow path.

An example of this is shown in FIG. 17, which shows a balloon-tipped catheter 1712 that has been deployed in the second bronchial passageway 1715, which supplies direct flow to the targeted lung region. A bronchial isolation device 510 is deployed in a segmental bronchus 1735 that is proximal to the second bronchial passageway 1715 in order to bronchially isolate the targeted lung region. The catheter 1712 is sealed within the bronchial passageway 1715 by inflating a balloon 1720 mounted on the catheter 1712. A second balloon-tipped catheter 1725 is deployed in the first bronchial passageway 1710 and sealed by inflating a balloon 1730. The first part 1728 of the two-part adhesive is then injected into the bronchial passageway 1715 via the catheter 1712 and the second part 1732 of the two-part adhesive is injected into the bronchial passageway 1710 via the catheter 1725. The first and second parts are injected in such a manner that they flow into the lung and meet at the collateral pathway comprised of the incomplete interlobar fissure 28. As a result of the contact between the first and second parts, they solidify within the interlobar fissure and thereby partially or entirely seal the interlobar fissure.

Once the adhesive has solidified, any remaining quantity of the first and second parts can be suctioned out of the lung. Alternately, the first and second parts could be absorbable by the body so that excess material need not be removed. The aforementioned technique for sealing the collateral flow pathway could also be performed prior to the implantation of the bronchial isolation device(s) 510.

Implanted Shunt Tubes

One of the major challenges with emphysematic patients is that certain bronchial passageways collapse during exhalation, thus leading to reduced flow through these lumens. This often results in trapped gas in certain regions of the lung that exhale air through the collapsed lumen. This in turn can lead to hyperinflation of the lung region, as well as compression of the healthy lung tissue that is adjacent to the lung region. One way of treating the hyperinflated lung region is to implant bronchial isolation devices, such as one-way or two-way valves, in the bronchial passageway that lead to the lung region in order to promote lung region collapse. However, the effectiveness of the bronchial isolation devices can be limited due to the reduced air flow during exhalation through the native bronchial passageways, especially if collateral flow is present.

One method of counteracting this effect is to implant one or more shunt tubes that are inserted through the bronchial passageways and into the targeted lung region comprised of a damaged lung region. The shunt tubes provide a clear flow path for exhaled air that is not be occluded by the collapsed bronchial passageway. In order to collapse the targeted lung region, one-way valves may be either mounted to a proximal end of the shunt tubes, or implanted in the bronchial passageways at some distance proximal to the proximal end of the tubes. These valves allow exhaled air to escape in the exhalation direction through the valve or valves, but do not allow inhaled air to return to the isolated targeted lung region. In this way, the targeted lung region eventually collapses after sufficient air had been exhaled. Alternatively, a self expanding braided tube can be used to prop the collapsed airway open. This allows side branches to continue to exhale air into the braided tube while keeping the bronchi open.

Figure 18:
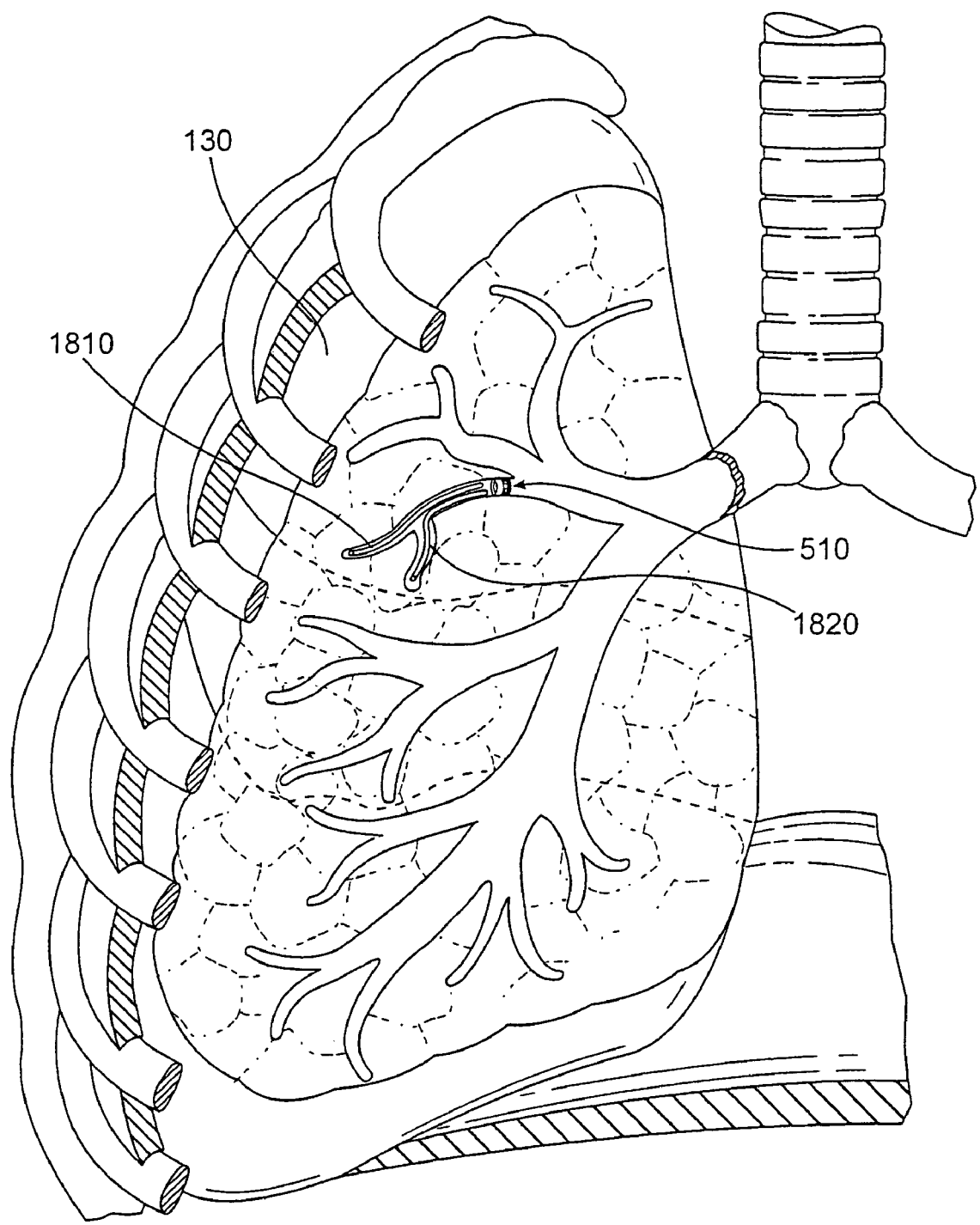
FIG. 18 illustrates the use of shunt tubes that are mounted in bronchial passageway to provide free air pathways to a targeted lung region.

FIG. 18 shows an example of how shunt tubes can be utilized. A bronchial isolation device 510 is implanted in a bronchial passageway of the right upper lobe 130. Two implanted shunt tubes 1810 and 1820 are shown deployed in two lumens. The shunt tubes 1810, 1820 are located distal to the implanted isolation device 510. The shunt tubes 1810, 1820 keep the airways open and provide a flow path through which exhaled air can pass. The implanted shunt tubes 1810 and 1820 are shown in FIG. 18 as being implanted just distally to the implanted bronchial isolation device 510. Alternatively, the shunt tubes may be implanted more distally, and a greater quantity may be implanted. The shunt tubes may be anchored in the bronchial lumen in a number of ways. In a first embodiment, the shunt tube have spring resilience and expand when released from a smaller constrained diameter to a larger diameter, thus gripping the bronchial lumen wall. Alternately, the shunt tubes may comprise a deformable retainer that is expanded to grip the bronchial lumen wall by inflating a balloon placed inside the collapsed shunt tube. The shunt tubes may also comprise a cylindrical structure that increases in diameter when its temperature is raised to body temperature. The shunt tubes may also have barbs, prongs or other features on the outside that assist in gripping the bronchial lumen wall for retention.

Exemplary Bronchial Isolation Devices

Figure 19:
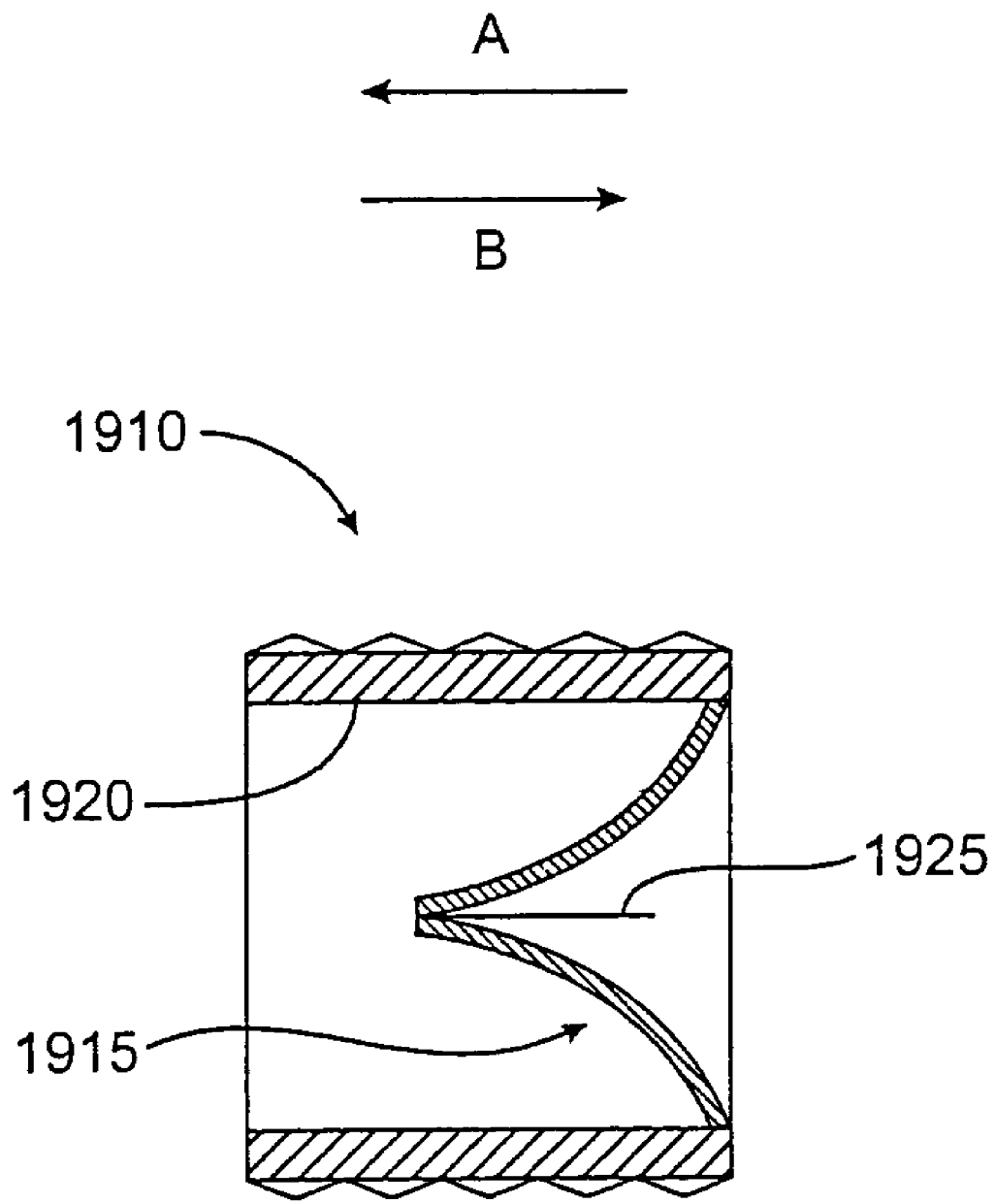
FIG. 19 is a cross-sectional view of a flow control element that allows fluid flow in a first direction but blocks fluid flow in a second direction.

As discussed above, a target lung region can be bronchially isolated by advancing a bronchial isolation device into the one or more bronchial pathways that directly feed air to the targeted lung region. The bronchial isolation device can be a device that regulates the flow of fluid into or out of a lung region through a bronchial passageway. FIG. 19 shows a cross-sectional view of an exemplary bronchial isolation device comprised of a flow control element 1910. It should be appreciated that the flow control element 1910 is merely an exemplary bronchial isolation device and that other types of bronchial isolation devices for regulating air flow can also be used. For example, the following references describe exemplary bronchial isolation devices: U.S. Pat. No. 5,954,766 entitled "Body Fluid Flow Control Device; U.S. patent application Ser. No. 09/797,910, entitled "Methods and Devices for Use in Performing Pulmonary Procedures"; and U.S. patent application Ser. No. 10/270,792, entitled "Bronchial Flow Control Devices and Methods of Use". The foregoing references are all incorporated by reference in their entirety and are all assigned to Emphasys Medical, Inc., the assignee of the instant application.

With reference to FIG. 19, the flow control element 1910 is in the form of a valve with a valve member 1915 supported by a ring 1920. The valve member 1915 is a duckbill-type valve and has two flaps defining an opening 1925. The valve member 1915 is shown in a flow-preventing orientation in FIG. 19 with the opening 1925 closed. The valve member 1915 is configured to allow free fluid flow in a first direction (along arrow A) while controlling fluid flow in a second direction (along arrow B). In the illustrated embodiment, fluid flow in the direction of arrow B is controlled by being completely blocked by valve member 1915. The first and second directions in which fluid flow is allowed and controlled, respectively, can be opposite or substantially opposite each other, such as is shown in FIG. 19. The valve member 1915 functions as a one-way valve by completely blocking fluid flow in a certain direction. It should be appreciated that the flow control element could be configured to block or regulate flow along two-directions.

Figure 20:
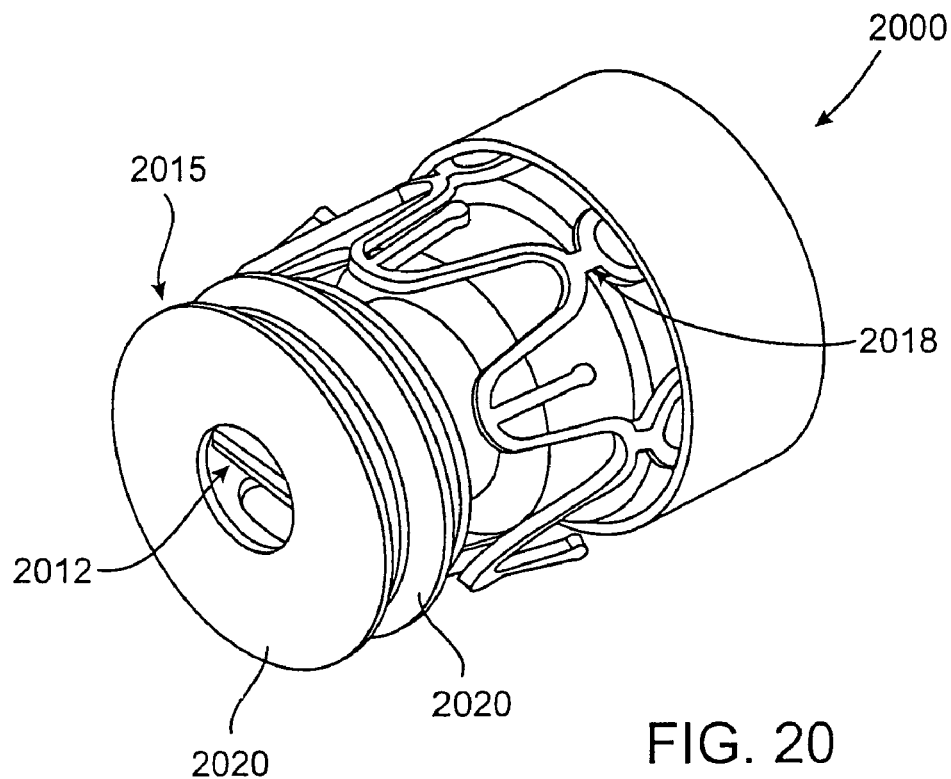
FIG. 20 shows a perspective view of another embodiment of a flow control element.
Figure 21:
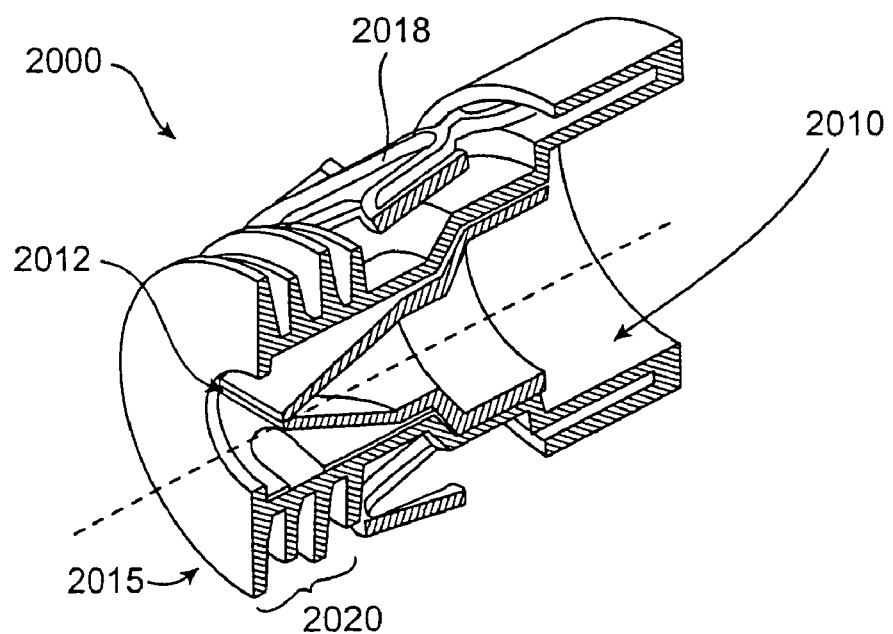
FIG. 21 shows a cross-sectional, perspective view of the flow control element of FIG. 21.

FIGS. 20 and 21 show another embodiment of an exemplary flow control element, comprising flow control element 2000. The flow control element 2000 includes a main body that defines an interior lumen 2010 through which fluid can flow along a flow path. The flow of fluid through the interior lumen 2010 is controlled by a valve member 2012. The valve member 2012 in FIGS. 20-21 is a one-way valve, although two-way valves can also be used, depending on the type of flow regulation desired. FIGS. 22-25 show an exemplary two-way valve member 2500.

With reference again to FIGS. 20-21, the flow control element 2010 has a general outer shape and contour that permits the flow control device 2010 to fit entirely within a body passageway, such as within a bronchial passageway. The flow control member 2000, includes an outer seal member 2015 that provides a seal with the internal walls of a body passageway when the flow control device is implanted into the body passageway. The seal member 2015 includes a series of radially-extending, circular flanges 2020 that surround the outer circumference of the flow control device 2000. The flow control device 2000 also includes an anchor member 2018 that functions to anchor the flow control device 2000 within a body passageway. It should be appreciated that other types of flow control devices can also be used to bronchially isolate the targeted lung region.

The flow control element can be implanted in the bronchial passageway using a delivery catheter. According to this process, the flow control element is mounted on a distal end of the delivery catheter. The distal end of the delivery catheter is then deployed to the bronchial passageway, such as by inserting the delivery catheter through the patient's mouth or nose, through the trachea, and through the bronchial tree to the desired location in the bronchial passageway. The delivery catheter can be deployed, for example, using a guide wire or without a guide wire. In one embodiment, a bronchoscope is deployed to the location in the bronchial passageway where the flow control device will be deployed. The delivery catheter with the flow control element is then deployed to the bronchial passageway by inserting the delivery catheter through a working channel of the bronchoscope such that the distal end of the delivery catheter and the attached flow control element protrude from the distal end of the working channel into the bronchial passageway. The flow control element is then removed from the delivery catheter so that the flow control elements is positioned within and retained in the bronchial passageway. U.S. patent application Ser. No. 10/270,792, entitled "Bronchial Flow Control Devices,and Methods of Use" (which is assigned to Emphasys Medical, Inc., the assignee of the instant application) describes various methods and devices for implanting a flow control element into a bronchial passageway.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. A method of regulating fluid flow for a targeted lung region, comprising:
   identifying a targeted lung region;
   implanting a first flow control element in a bronchial passageway that provides direct fluid flow to the targeted lung region;
   identifying at least one collateral pathway that provides collateral fluid flow to the targeted lung region; and
   performing an intervention within the lung to substantially prevent the identified collateral pathway from providing collateral fluid flow to the targeted lung region, wherein performing an intervention comprises inserting a glue into the lung to at least partially seal the collateral pathway.

2. A method of regulating fluid flow for a targeted lung region, comprising:
   identifying a targeted lung region;
   implanting a first flow control element in a bronchial passageway that provides direct fluid flow to the targeted lung region;
   identifying at least one collateral pathway that provides collateral fluid flow to the targeted lung region; and
   performing an intervention within the lung to substantially prevent the identified collateral pathway from providing collateral fluid flow to the targeted lung region, wherein performing an intervention comprises inserting a sclerosing agent into the lung to cause sclerosis in lung tissue.

3. A method of regulating fluid flow for a targeted lung region, comprising:
   identifying a targeted lung region;
   implanting a first flow control element in a bronchial passageway that provides direct fluid flow to the targeted lung region;
   identifying at least one collateral pathway that provides collateral fluid flow to the targeted lung region; and
   performing an intervention within the lung to substantially prevent the identified collateral pathway from providing collateral fluid flow to the targeted lung region, wherein performing an intervention comprises inserting a fibrosing agent in the lung to promote fibrosis in the lung tissue.

4. A method of regulating fluid flow for a targeted lung region, comprising:
   identifying a targeted lung region;
   implanting a first flow control element in a bronchial passageway that provides direct fluid flow to the targeted lung region;
   identifying at least one collateral pathway that provides collateral fluid flow to the targeted lung region; and
   performing an intervention within the lung to substantially prevent the identified collateral pathway from providing collateral fluid flow to the targeted lung region, wherein performing an intervention comprises inserting a foam into the lung, wherein the foam expands to occlude the collateral pathway.

5. A method of regulating fluid flow for a targeted lung region, comprising:
   identifying a targeted lung region;
   implanting a first flow control element in a bronchial passageway that provides direct fluid flow to the targeted lung region;

identifying at least one collateral pathway that provides collateral fluid flow to the targeted lung region; and performing an intervention within the lung to substantially prevent the identified collateral pathway from providing collateral fluid flow to the targeted lung region, wherein performing an intervention comprises:
  (a) deploying a delivery catheter through a bronchial tree into the targeted lung region such that a distal end of the delivery catheter is positioned near the targeted lung region;
  (b) puncturing a bronchial wall of a bronchial passageway located near the targeted lung region;
  (c) passing the distal end of the delivery catheter through the bronchial wall into the target lung region; and
  (d) flowing a therapeutic agent through the delivery catheter so that the flowable therapeutic agent exits the distal end of the delivery catheter into the targeted lung region.

6. A method of regulating fluid flow for a targeted lung region, comprising:

identifying a targeted lung region;

implanting a first flow control element in a bronchial passageway that provides direct fluid flow to the targeted lung region;

identifying at least one collateral pathway that provides collateral fluid flow to the targeted lung region; and performing an intervention within the lung to substantially prevent the identified collateral pathway from providing collateral fluid flow to the targeted lung region, wherein performing an intervention comprises applying energy to lung tissue, wherein the energy induces a reaction in lung tissue that substantially prevents collateral flow into the targeted lung region.

* * * * *